(12) United States Patent
Pratt et al.

(10) Patent No.: US 7,083,655 B2
(45) Date of Patent: Aug. 1, 2006

(54) HAIR DYE COMPOSITION

(75) Inventors: Dominic Pratt, Darmstadt (DE); Toshio Kawagishi, Minamiashigara (JP)

(73) Assignees: Kao Corporation, Tokyo (JP); Fuji Photo Film Co., Ltd., Minamiashigara (JP)

( * ) Notice: Subject to any disclaimer, the term of this patent is extended or adjusted under 35 U.S.C. 154(b) by 276 days.

(21) Appl. No.: 10/445,819

(22) Filed: May 28, 2003

(65) Prior Publication Data

US 2004/0019982 A1 Feb. 5, 2004

(30) Foreign Application Priority Data

May 28, 2002 (EP) ................... 02011605

(51) Int. Cl.
*A61K 7/13* (2006.01)
(52) U.S. Cl. .................. 8/405; 8/407; 8/437; 8/451; 8/463; 8/466; 8/570; 8/573; 8/574; 548/400; 546/1
(58) Field of Classification Search .................. 8/405, 8/407, 437, 451, 463, 466, 570, 573, 574; 548/400; 546/1
See application file for complete search history.

(56) References Cited

U.S. PATENT DOCUMENTS

| 4,055,556 A | 10/1977 | Aeberli | 534/794 |
| 5,324,826 A * | 6/1994 | Matzinger | 534/794 |
| 5,637,115 A * | 6/1997 | Balzer et al. | 8/407 |
| 5,691,458 A | 11/1997 | Arnost et al. | 534/774 |
| 5,889,163 A | 3/1999 | Takeuchi et al. | 534/586 |

FOREIGN PATENT DOCUMENTS

| DE | 100 28 686 | 12/2001 |
| GB | 1 296 857 | 11/1972 |

OTHER PUBLICATIONS

Chemical Abstract, AN 71:62277, XP-002219140, JP 44-008119, Apr. 16, 1969.
R. N. Shreve, et al., Journal of the American Chemical Society, vol. 65, pp. 2241-2243, XP-002219139, "Studies in AZO Dyes. I. Preparation and Bacteriostatic Properties of AZO Derivatives of 2,6-Diaminopyridine", 1943.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The present invention is directed to a hair dyeing composition comprising at least one azo dye of the following general formula (1):

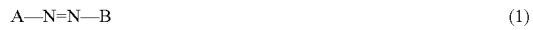

where A=monovalent, optionally substituted heterocyclic group binding via the carbon atom to the azo group, that does not contain carboxy ($-CO_2H$) or sulfo groups ($SO_3H$) or quaternary ammonium groups and B=heterocyclic, aromatic or alkyl group containing a dissociative proton and, which is free of carboxy ($-CO_2H$) or sulfo groups ($-SO_3H$) or quaternary ammonium groups. Additionally, the present invention describes a method of dyeing human or animal hair by using such a dye and the use of this direct azo dye for dyeing human or animal hair. The use of this direct azo dye can impart the hair with an extremely vivid colour and has a less colour fade over the time.

9 Claims, No Drawings

HAIR DYE COMPOSITION

TECHNICAL FIELD

The present invention relates to a hair dye composition that provides high dyeing power, can strongly impart the hair with extremely vivid colour, has less colour fade over time and can deliver a wide range of colours.

BACKGROUND ART

Hair dyes can be classified by the dye to be used or by whether they have any bleaching action on melanin. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and at least one direct dye such as an acid dye, a basic dye or a nitro dye.

The above-described permanent hair dye is however accompanied with the drawbacks that the colour tone imparted by an oxidation dye is not so vivid and that the colour of the hair dyed with a vivid-colour producing nitro dye ordinarily employed as a direct dye markedly fades over time and becomes dull quickly even if the colour tone immediately after dyeing is very vivid (Japanese Patent Application Laid-Open (Kokai) No. Hei 6-271435).

It is common practice to combine direct dyes and oxidative dyes in permanent products to provide more vivid colour, however currently available direct dyes do not usually perform satisfactorily. The number of direct dyestuff that can be used in combination with oxidative dyes is limited by the necessity that they must be stable to alkaline peroxide during the dyeing process.

A variety of cationic direct dyes and nitro dyes have been used in permanent hair dye products to add brilliance and vividness to shades. However, in both cases the colour fades very quickly due to the loss of the direct dye from washing and light, especially on damaged or porous hair.

DISCLOSURE OF THE INVENTION

An object of the present invention is to provide a hair dye composition comprising a dissociative azo dye which can strongly impart the hair with a vivid colour without decomposition of the dye upon hair dyeing, has excellent resistance to light, washing, perspiration, friction and heat, is stable against an alkalising agent and an oxidizing agent, has high hair dyeing power and shows less colour fade over time.

Another object is to provide a hair dyeing method by applying the above mentioned azo dye to the hair.

The present inventors have found that dissociative azo dyes of the general structure (1) below and the resulting dyeing composition can strongly impart the hair with a vivid colour selected from a wide range of different colours without decomposition of the dye upon hair dyeing, and exhibits excellent resistance to fading from light, washing, perspiration, friction and heat.

In one aspect of the present invention, there is thus provided a hair dye composition comprising an azo dye represented by the following general formula (1):

General Formula (1)

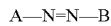

(1)

where "A" represents a monovalent optionally substituted hetero-ring binding via the carbon atom to the azo group that does not contain a carboxy, sulfo or quaternary ammonium group; and "B" represents an atomic group required for the compound represented by the general formula (1) to form a dissociative azo dye, more specifically a heterocyclic, aromatic or alkyl group containing a dissociative proton, which is free of carboxy, sulfo or quaternary ammonium groups.

Neither of "A" and "B" in formula (1) contains any of carboxy, sulfo and quaternary ammonium group. The carboxy or sulfo group herein includes, in addition to the acid type groups, neutral type groups such as —COONa or —SO$_3$Na. In other words, azo dye (1) contains neither the acid or neutral type carboxy or sulfo group nor quaternary ammonium group, and is neither anionic nor cationic.

The monovalent hetero-ring group represented by "A" is preferably a 5-membered or 6-membered hetero-ring including at least one hetero atom selected from oxygen atom, sulfur atom or nitrogen atom within the ring. More preferably, the monovalent hetero-ring is an aromatic hetero-ring. The monovalent hetero-ring represented by "A" may be a ring condensed with another ring. Among such condensed groups, preferably, ring-condensed groups with a 5-membered or 6-membered ring are preferable. The number of carbon atoms in the hetero-ring that may include substituents on the hetero-ring, is preferably 2 to 20, more preferably 2 to 10.

The monovalent hetero-ring group represented by "A" is preferably derived from a diazo component.

Herein, the diazo component means a partial structure introduced by converting a hetero-ring compound containing an amino substituent to a diazo compound, subjecting a diazo-coupling reaction with the resulting diazo compound and a coupler, which belongs to a concept commonly used in the field of azo dyes.

In other words, hetero-ring group represented by "A" is a substituent prepared by eliminating an amino group from an amino-substituted hetero-ring compound possibly subjected to diazo reaction, to render the resulting product that is a monovalent group.

In the general formula (1), the hetero-ring group represented by "A" may contain one or more substituents, wherein 2 or more substituents may be the same or different groups. Examples of the substituents include for example halogen atom, alkyl group (including cycloalkyl group), alkenyl group (including cycloalkenyl group), alkynyl group, aryl group, hetero-ring group, cyano group, hydroxyl group, nitro group, alkoxyl group, aryloxy group, silyloxy group, hetero-ring oxy group, acyloxy group, carbamoyloxy group, alkoxycarbonyloxy group, aryloxycarbonyloxy, amino group (including anilino group), acylamino group, aminocarbonylamino group, alkoxycarbonylamino group, aryloxycarbonylamino group, sulfamoylamino group, alkylsulfonylamino group, arylsulfonylamino group, mercapto group, alkylthio group, arylthio group, hetero-ring thio group, sulfamoyl group, alkylsulfinyl group, arylsulfinyl group, alkylsulfonyl group, arylsulfonyl group, acyl group, alkoxycarbonyl group, aryloxycarbonyl group, carbamoyl group, arylazo group, hetero-ring azo group, imide group, phosphino group, phosphinyl group, phosphinyloxy group, phosphinylamino group, and silyl group. More specifically, the substituent includes for example halogen atom (for example, chlorine atom, bromine atom, iodine atom), alkyl group (linear or branched or cyclic alkyl group with one to 10 carbon atoms, preferably one to 6 carbon atoms, for example, methyl, ethyl, n-propyl, isopropyl, t-butyl, n-octyl, 2-chloroethyl, 2-cyanoethyl, 2-ethylhexyl, cyclopropyl, cyclopentyl), alkenyl group (linear or branched or cyclic alkenyl group with 2 to 10 carbon atoms, preferably 2 to 6 carbon atoms, for example, vinyl, allyl, prenyl, cyclopenten-1-yl), alkynyl group (alkynyl group with 2 to 10 carbon atoms, preferably 2 to 6 carbon atoms, for example, ethynyl, propargyl), aryl group (aryl group with 6 to 12 carbon atoms, preferably 6 to 8 carbon atoms, for example, phenyl, p-tolyl, naphthyl, 3-chlorophenyl, 2-aminophenyl), hetero-ring group (monovalent group with one to 12 carbon atoms, preferably 2 to 6 carbon atoms, which is recovered by eliminating one hydrogen atom from an aromatic or non-aromatic 5-membered or 6-membered hetero-ring compound; for example, 1-pyrazolyl, 1-imidazolyl, 2-furyl, 2-thienyl, 4-pyrimidinyl, 2-benzothiazolyl), cyano group, hydroxyl group, nitro group, alkoxy group (linear or branched or cyclic alkoxy group with one to 10 carbon atoms, preferably one to 6 carbon atoms, for example, methoxy, ethoxy, isopropoxy, t-butoxy, cyclopentyloxy, 2-buten-1-yloxy, 2-methoxyethoxy), aryloxy group (aryloxy group with 6 to 12 carbon atoms, preferably 6 to 8 carbon atoms, for example, phenoxy, 2-methylphenoxy, 4-t-butylphenoxy, 3-nitrophenoxy), silyloxy group (silyloxy group with 3 to 10 carbon atoms, preferably 3 to 6 carbon atoms, for example, trimethylsilyloxy, t-butyldimethylsilyloxy), hetero-ring oxy group (hetero-ring oxy group with one to 12 carbon atoms, preferably 2 to 6 carbon atoms, for example, 1-phenyltetrazole-5-oxy, 2-tetrahydropyranyloxy), acyloxy group (acyloxy group with one to 12 carbon atoms, preferably one to 8 carbon atoms, for example, formyloxy group, acetyloxy, pivaloyloxy, benzoyloxy, p-methoxyphenylcarbonyloxy), carbamoyloxy group (carbamoyloxy group with one to 10 carbon atoms, preferably one to 6 carbon atoms, for example, N,N-dimethylcarbamoyloxy, N,N-diethylcarbamoyloxy, morpholinocarbonyloxy, N-n-octylcarbamoyloxy), alkoxycarbonyloxy group (alkoxycarbonyloxy group with 2 to 10 carbon atoms, preferably 2 to 6 carbon atoms, for example, methoxycarbonyloxy, ethoxycarbonyloxy, t-butoxycarbonyloxy, n-octyloxycarbonyloxy), aryloxycarbonyloxy group (aryloxycarbonyloxy group with 7 to 12 carbon atoms, preferably 7 to 10 carbon atoms, for example, phenoxycarbonyloxy, p-methoxyphenoxycarbonyloxy), amino group (amino group, alkylamino group with one to 10 carbon atoms, preferably one to 6 carbon atoms, anilino group with 6 to 12 carbon atoms, preferably 6 to 8 carbon atoms, or hetero-ring amino group with one to 12 carbon atoms, preferably 2 to 6 carbon atoms, including for example amino, methylamino, dimethylamino, anilino, N-methyl-anilino, diphenylamino, imidazol-2-ylamino, pyrazol-3-ylamino), acylamino group (alkylcarbonylamino group with one to 10 carbon atoms, preferably one to 6 carbon atoms, arylcarbonylamino group with 6 to 12 carbon atoms, preferably 6 to 8 carbon atoms, or hetero-ring carbonylamino group with 2 to 12 carbon atoms, preferably 2 to 6 carbon atoms, including for example formylamino, acetylamino, pivaloylamino, benzoylamino, pyridine-4-carbonylamino, thiophene-2-carbonylamino), aminocarbonylamino group (aminocarbonylamino with one to 12 carbon atoms, preferably one to 6 carbon atoms, for example, carbamoylamino, N,N-dimethylaminocarbonylamino, N,N-diethylaminocarbonylamino, morpholin-4-ylcarbonylamino), alkoxycarbonylamino group (alkoxycarbonylamino group with 2 to 10 carbon atoms, preferably 2 to 6 carbon atoms, for example, methoxycarbonylamino, ethoxycarbonylamino, t-butoxycarbonylamino), aryloxycarbonylamino group (aryloxycarbonylamino group with 7 to 12 carbon atoms, preferably 7 to 9 carbon atoms, for example, phenoxycarbonylamino, p-chlorophenoxycarbonylamino, 4-methoxyphenoxycarbonylamino), sulfamoylamino group (sulfamoylamino group with zero to 10 carbon atoms, preferably zero to 6 carbon atoms, for example sulfamoylamino, N,N-dimethylaminosulfonylamino, N-(2-hydroxyethyl)sulfamoylamino), alkylsulfonylamino group (alkylsulfonylamino group with one to 10 carbon atoms, preferably one to 6 carbon atoms, for example, methylsulfonylamino, butylsulfonylamino), arylsulfonylamino group (arylsulfonylamino group with 6 to 12 carbon atoms, preferably 6 to 8 carbon atoms, for example, phenylsulfonylamino, 2,3,5-trichlorophenylsulfonylamino, p-methylphenylsulfonylamino), mercapto group, alkylthio group (alkylthio group with one to 10 carbon atoms, preferably one to 6 carbon atoms, for example methylthio, ethylethio, butylthio), arylthio group (arylthio with 6 to 12 carbon atoms, preferably 6 to 8 carbon atoms, for example, phenylthio, p-chlorophenylthio, m-methoxythio), hetero-ring thio group (hetero-ring thio group with 2 to 10 carbon atoms, preferably one to 6 carbon atoms, for example 2-benzothiazolylthio, 1-phenyltetrazol-5-ylthio), sulfamoyl group (sulfamoyl group with zero to 10 carbon atoms, preferably zero to 6 carbon atoms, for example, sulfamoyl, N-ethylsulfamoyl, N,N-dimethylsulfamoyl, N-acetylsulfamoyl, N-benzoylsulfamoyl), alkylsulfinyl group (alkylsulfinyl group with one to 10 carbon atoms, preferably one to 6 carbon atoms, for example, methylsulfinyl, ethylsulfinyl), arylsulfinyl group (arylsulfinyl group with 6 to 12 carbon atoms, preferably 6 to 8 carbon atoms, for example, phenylsulfinyl, p-methylphenylsulfinyl), alkylsulfonyl group (alkylsulfonyl group with one to 10 carbon atoms, preferably one to 6 carbon atoms, for example, methylsulfonyl, ethylsulfonyl), arylsulfonyl group (arylsulfonyl group with 6 to 12 carbon atoms, preferably 6 to 8 carbon atoms, for example, phenylsulfonyl, p-chlorophenylsulfonyl), acyl group (formyl group, alkylcarbonyl group with 2 to 10 carbon atoms, preferably 2 to 6 carbon atoms, or arylcarbonyl group with 7 to 12 carbon atoms, preferably 7 to 9 carbon atoms, including for example acetyl, pivaloyl, 2-chloroacetyl, benzoyl, 2,4-dichlorobenzoyl), alkoxycarbonyl group (alkoxycarbonyl group with 2 to 10 carbon atoms, preferably 2 to 6 carbon atoms, for example, methoxycarbonyl, ethoxycarbonyl, t-butoxycarbonyl, isobutyloxycarbonyl), aryloxycarbonyl group (aryloxycarbonyl group with 7 to 12 carbon atoms, preferably 7 to 9 carbon atoms, for example, phenoxycarbonyl, 2-chlorophenoxycarbonyl, 3-nitrophenoxycarbonyl, 4-t-butylphenoxycarbonyl), carbamoyl group (carbamoyl group with one to 10 carbon atoms, preferably one to 6 carbon atoms, for example, carbamoyl, N-methylcarbamoyl, N,N-dimethylcarbamoyl, N-(2-hydroxyethyl)carbamoyl, N-(methylsulfonyl)carbamoyl), arylazo group (arylazo group with 6 to 12 carbon atoms, preferably 6 to 8 carbon atoms, for example phenylazo, p-chlorophenylazo), hetero-ring azo group (hetero-ring azo group with one to 10 carbon atoms, preferably one to 6 carbon atoms, for example, pyrazol-3-ylazo, thiazol-2-ylazo, 5-ethylthio-1,3,4-thiadiazol-2-ylazo), imide group (imide group with 2 to 10 carbon atoms, preferably 4 to 8 carbon atoms, for example, N-succinimide, N-phthalimide), phosphino group (phosphino group with 2 to 12 carbon atoms, preferably 2 to 6 carbon atoms, for example, dimethylphosphino, diphenylphosphino, methylphenoxyphosphino), phosphinyl group (phosphinyl group with 2 to 12 carbon atoms, preferably 2 to 6 carbon atoms, for example phosphinyl, diethoxyphosphinyl), phosphinyloxy group (phosphinyloxy group with 2 to 12 carbon atoms, preferably 2 to 6 carbon atoms, for example, diphenoxyphosphinyloxy, dibutoxyphosphinyloxy), phosphinylamino group (phosphinylamino group with 2 to 12 carbon atoms, preferably 2 to 6 carbon atoms, for example, dimethoxyphosphinylamino, dimethylaminophosphinylamino), and silyl group (silyl group with 3 to 12 carbon atoms, preferably 3 to 8 carbon atoms, for example, trimethylsilyl, t-butyldimethylsilyl, phenyldimethylsilyl). In case that these groups are groups with a possibility of additional substitution, these groups may further contain substituents, and preferably, such substituents then include the groups with the same meaning as described as the preferable substituent for the hetero-ring group represented by A. In case that these groups are substituted with 2 or more substituents, the substituents may be the same or different.

Particularly preferably, the substituent for the hetero-ring group represented by A is halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably, the substituent is halogen atom, alkyl group, cyano group, hydroxyl group, nitro group, alkoxy group, amino group (including anilino group), acylamino group, alkylsulfonylamino group and carbamoyl group.

Specific examples (A-1) to (A-25) of the monovalent hetero-ring group binding via the carbon atom to the azo group, as represented by "A" in the general formula (1), are described below, but the invention is not at all limited thereto.

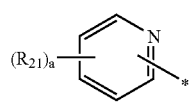 (A-1)

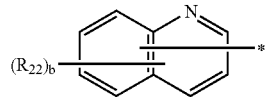 (A-2)

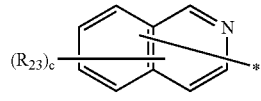 (A-3)

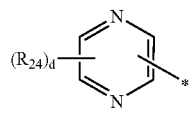 (A-4)

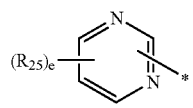 (A-5)

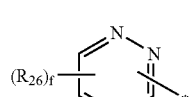 (A-6)

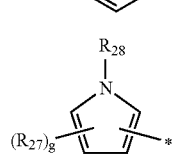 (A-7)

-continued

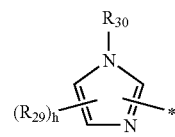 (A-8)

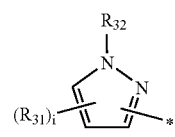 (A-9)

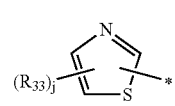 (A-10)

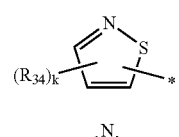 (A-11)

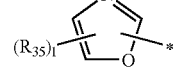 (A-12)

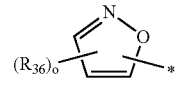 (A-13)

 (A-14)

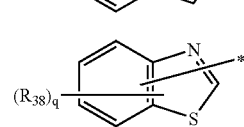 (A-15)

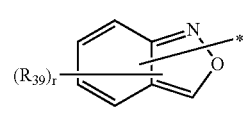 (A-16)

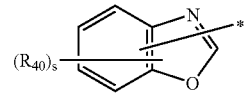 (A-17)

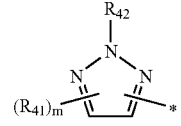 (A-18)

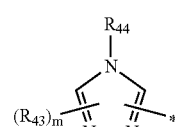 (A-19)

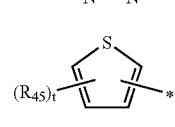 (A-20)

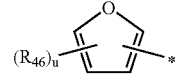 (A-21)

-continued

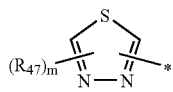 (A-22)

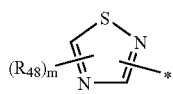 (A-23)

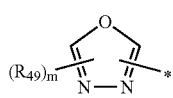 (A-24)

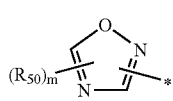 (A-25)

In the specific examples (A-1) to (A-25), the symbol "*" expresses the position in the general formula (1), at which the hetero-ring group binds to the azo group; $R_{21}$ to $R_{50}$ independently represent hydrogen atom or a substituent. The substituent represents a group with the same meaning, as listed as the substituent for the hetero-ring group represented by A, and the substituent preferably includes halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably, the substituent is halogen atom, alkyl group, cyano group, hydroxyl group, nitro group, alkoxy group, amino group (including anilino group), acylamino group, alkylsulfonylamino group, and carbamoyl group. "a, p, q, r, s" represent an integer of 0 to 4. "b, c" represent an integer of 0 to 6. "d, e, f, g, t, u" represent an integer of 0 to 3. "h, i, j, k, l, o" represent an integer of 0 to 2. "m" represent an integer of 0 to 1. When "a" to "u" represent an integer of 2 or more, groups represented by $R_{21}$ to $R_{50}$, which exist in a number of 2 or more, may be the same or different to each other.

Further, groups adjacent to each other as represented by $R_{21}$ to $R_{50}$ may combine together to form a ring structure. The resulting ring structure formed may be a hetero-ring or a carbon ring, and it may be a saturated ring or an unsaturated ring. The total number of the carbon atoms and the hetero atoms is 3 to 6, preferably 5 or 6.

In case that $R_{21}$ to $R_{50}$ in the formulas (A-1) to (A-25) are groups with a possibility of additional substitution, $R_{21}$ to $R_{50}$ may further contain a substituent and the substituent in that case is the same as listed as the substituent for the hetero-ring group represented by "A".

In the compound represented by the general formula (1) in accordance with the invention, the hetero-ring group represented by A is preferably (A-1), (A-5), (A-8), (A-9), (A-10), (A-11), (A-12), (A-13), (A-14), (A-15), (A-17), (A-19), (A-22), (A-23), (A-24), and (A-25), more preferably (A-10), (A-11), (A-12), (A-14), (A-22), (A-23), and (A-25).

B in the azo dye represented by the general formula (1) represents an atomic group essential for the formation of a dissociative azo dye from the compound represented by the general formula (1) and is preferably derived from a coupler component. Herein, the coupler component means a partial structure derived from a coupler compound capable of reacting with a diazonium salt to give an azo dye. The concept is commonly used in the field of azo dye. B in the azo dye represented by the general formula (1) has preferably 3 to 30 carbon atoms, more preferably 3 to 20 carbon atoms, most preferably 3 to 12 carbon atoms, inclusive of the substituents therein.

Preferably B is a 5 or 6 membered heterocyclic or heterocyclic condensed ring, containing at least one heteroatom selected from sulfur, nitrogen and oxygen atom; a 5 or 6 membered optionally condensed aromatic ring, a $C_{1-6}$-alkyl, $C_{2-6}$-alkenyl or $C_{2-6}$-alkynyl group wherein these groups optionally contain α-CO-group, wherein each of the above rings or groups may contain one or more substituent(s).

The coupler component is preferably a coupler component known in the field of silver halide colour photographic materials, and as such, use can be made of the backbone moiety of a coupler for silver halide colour photographic materials (the moiety serving as a dye chromophore via coupling with an oxidized aromatic amine-based developer as a principal developing agent, such as p-phenylenediamine), which is described in detail in Research Disclosure 37038 (February 1995), page 80–85, and 87–89.

The coupler known as a coupler forming yellow-coloured image in the field of silver halide colour photographic materials includes for example couplers of pivaloylacetamide type, benzoylacetamide type, malondiester type, malondiamide type, dibenzoylmethane type, benzothiazolylacetamide type, malonestermonoamide type, benzoxazolylacetamide type, benzimidazolylacetamide type, cyanoacetamide type, cycloalkylcarbonylacetamide type, indolin-2-ylacetamide type, quinazolin-4-on-2-ylacetamide type described in U.S. Pat. No. 5,021,332, the benzo-1,2,4-thiadiazine-1,1,-dioxid-3-ylacetamide type described in U.S. Pat. No. 5,021,330, the coupler described in EP 421221A, the coupler described in U.S. Pat. No. 5,455,149, the coupler described in EP 0622673A, the couplers of 3-indoloylacetamide type described in EP 0953871A, 0953872A and 0953873A, as preferable coupler backbones.

The coupler known as a coupler forming magenta-coloured image in the field of silver halide colour photographic materials includes for example couplers of 5-pyrazolone type, 1H-pyrazolo[1,5-a]benzimidazole type, 1H-pyrazolo[5,1-c][1,2,4]triazole type, 1H-pyrazolo[1,5-b][1,2,4]triazole type, 1H-imidazo[1,2-b]pyrazole type, cyanoacetophenone type, the active propene type described in WO 93/01523, and the enamine type described in WO 93/07534, the 1H-imidazo[1,2-b][1,2,4]triazole type coupler and the coupler described in U.S. Pat. No. 4,871,652, as preferable coupler backbones.

The coupler known as a coupler forming cyan-coloured image in the field of silver halide colour photographic materials includes for example couplers of phenol type, naphthol type, the 2,5-diphenylimidazole type, 1H-pyrrolo[1,2-b][1,2,4]triazole type, and 1H-pyrrolo[2,1-c][1,2,4]triazole type as described in EP 0249453A, the pyrrole type described in Japanese Patent Laid-open Nos. 188137/1992 and 190347/1992, 3-hydroxypyridine type described in Japanese Patent Laid-open No. 315736/1989, pyrrolopyrazole type described in U.S. Pat. No. 5,164,289, the pyrroloimidazole type described in Japanese Patent Laid-open No. 174429/1992, and the pyrazolopyrimidine type described in U.S. Pat. No. 4,950,585, and the pyrrolotriazine type coupler described in Japanese Patent Laid-open No.

204730/1992, the coupler described in U.S. Pat. No. 4,746,602, the coupler described in U.S. Pat. No. 5,104,783, the coupler described in U.S. Pat. No. 5,162,196, and the coupler described in EP 0556700A, as preferable coupler backbones.

The group represented by B in the azo dye represented by the general formula (1) preferably includes groups represented by the following structures (B-1) to (B-12).

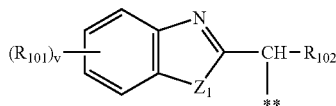
(B-1)

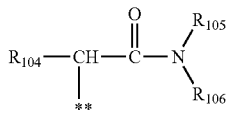
(B-2)

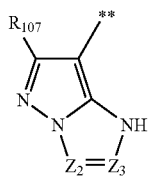
(B-3)

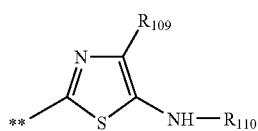
(B-4)

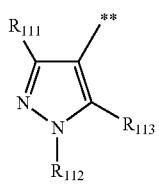
(B-5)

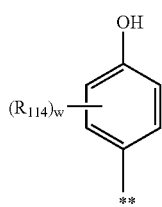
(B-6)

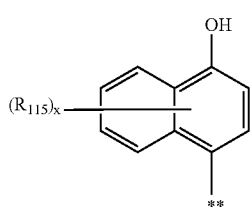
(B-7)

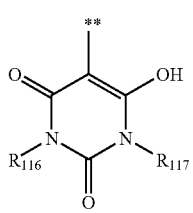
(B-8)

-continued

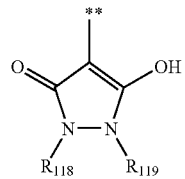
(B-9)

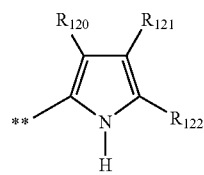
(B-10)

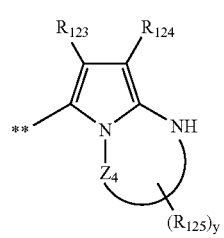
(B-11)

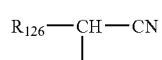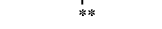
(B-12)

In the formulas, the symbol "**" expresses the position where the groups bind to the azo group in the general formula (1).

In the formula (B-1), $R_{101}$ represents halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group. $R_{102}$ represents cyano group, alkylsulfonyl group, arylsulfonyl group, acyl group, alkoxycarbonyl group, aryloxycarbonyl group, or carbamoyl group. $Z_1$ represents oxygen atom, sulfur atom, or —N($R_{103}$)—. $R_{103}$ represents hydrogen atom, alkyl group, aryl group or hetero-ring group. "v" represents an integer of 0 to 4. Provided that v is more than 1, the $R_{101}$ groups in the number "v" may be the same or different. $R_{101}$ is preferably halogen atom, acylamino group, alkylsulfonylamino group, sulfamoyl group, and carbamoyl group. $R_{102}$ is preferably cyano group, and carbamoyl group. $Z_1$ is preferably oxygen atom, sulfur atom, or —N($R_{103}$)— where $R_{103}$ is an alkyl group.

In the formula (B-2), $R_{104}$ represents cyano group, alkylsulfonyl group, arylsulfonyl group, acyl group, alkoxycarbonyl group, aryloxycarbonyl group, or carbamoyl group; $R_{105}$ and $R_{106}$ independently represent hydrogen atom, alkyl group, aryl group, or hetero-ring group. Preferably, $R_{104}$ is cyano group, acyl group, and carbamoyl group, while one of $R_{105}$ and $R_{106}$ is preferably hydrogen atom.

In the formula (B-3), $R_{107}$ represents hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)═ or —N═; $R_{108}$ represents alkyl group, aryl group, hetero-ring group, alkylthio group, arylthio group, alkoxycarbonyl group, or carbamoyl group. Provided that $Z_2$ and $Z_3$ both represent —C($R_{108}$)=, two $R_{108}$ groups may be the same or different or may bind together to form a carbon ring or a hetero-ring. $R_{107}$ is preferably hydrogen atom, alkyl group and aryl group, more preferably hydrogen atom and alkyl group, and $R_{108}$ is preferably alkyl group, aryl group, and hetero-ring group, more preferably alkyl group.

In the formula (B-4), $R_{109}$ represents alkyl group, aryl group or hetero-ring group, and $R_{110}$ represents hydrogen atom, alkyl group, aryl group, hetero-ring group, acyl group, alkylsulfonyl group or arylsulfonyl group. $R_{109}$ is preferably alkyl group and aryl group, and $R_{110}$ is preferably hydrogen atom and alkyl group.

In the formula (B-5), $R_{111}$ represents alkyl group, aryl group, alkoxy group, amino group (including anilino group), alkoxycarbonyl group, cyano group, acylamino group, or carbamoyl group; $R_{112}$ represents hydrogen atom, alkyl group, aryl group, or hetero-ring group; $R_{113}$ represents hydroxyl group or amino group. $R_{111}$ is preferably alkoxycarbonyl group, cyano group, and carbamoyl group; $R_{112}$ is preferably alkyl group and aryl group.

In the formula (B-6), $R_{114}$ represents halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, heteroring thio group, alkoxycarbonyl group, or carbamoyl group; "w" represents an integer of 0 to 4. Provided that "w" is 2 to 4, the $R_{114}$ groups may be the same or different. $R_{114}$ is preferably halogen atom, alkyl group, acylamino group, alkoxycarbonyl group, aminocarbonylamino group, alkylsulfonylamino group, arylsulfonylamino group, and carbamoyl group, more preferably halogen atom, alkyl group, acylamino group, and alkylsulfonylamino group.

In the formula (B-7), $R_{115}$ represents halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, heteroring thio group, alkoxycarbonyl group, or carbamoyl group; "x" represents an integer of 0 to 6. Provided that "x" is 2 to 6, the $R_{115}$ groups may be the same or different. $R_{115}$ is preferably halogen atom, acylamino group, alkoxycarbonylamino group, aminocarbonylamino group, alkylsulfonylamino group, arylsulfonylamino group, and carbamoyl group, more preferably acylamino group, alkylsulfonylamino group, and carbamoyl group.

In the formula (B-8), $R_{116}$ and $R_{117}$ independently represent alkyl group or aryl group, and these groups are preferably the same to each other.

In the formula (B-9), $R_{118}$ and $R_{119}$ independently represent alkyl group or aryl group, and these groups are preferably the same to each other.

In the formula (B-10), $R_{120}$ and $R_{121}$ independently represent alkyl group, aryl group, hetero-ring group, cyano group, alkylsulfonyl group, arylsulfonyl group, alkoxycarbonyl group, or carbamoyl group; $R_{122}$ represents hydrogen atom, alkyl group, aryl group, hetero-ring group, acylamino group, alkylsulfonylamino group, or arylsulfonylamino group. Preferably, $R_{120}$ and $R_{121}$ are alkyl group, aryl group, hetero-ring group, and cyano group. Preferably, $R_{122}$ is hydrogen atom, alkyl group, aryl group, acylamino group, and alkylsulfonylamino group.

In the formula (B-11), $R_{123}$ and $R_{124}$ independently represent alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and one carbon atom. $R_{125}$ represents alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of 0 to 2, provided that $Z_4$ forms a 5-membered ring; and "y" represents an integer of 0 to 3, provided that $Z_4$ forms a 6-membered ring. Preferably, $R_{123}$ is alkyl group, aryl group, hetero-ring group, and cyano group. Preferably, $R_{124}$ is alkylsulfonyl group, arylsulfonyl group, alkoxycarbonyl group, and carbamoyl group. $R_{125}$ is preferably alkyl group, aryl group, alkylthio group, amino group, and acylamino group. In the formula (B-12), $R_{126}$ represents alkyl group or aryl group In the formulas (B-1) to (B-12), preferable carbon numbers and specific examples of the individual groups listed in the descriptions of the groups represented by $R_{101}$ to $R_{125}$ are the same as those listed in the description of the substituent for the hetero-ring group represented by A.

In case that $R_{101}$ to $R_{126}$ in the formulas (B-1) to (B-12) are groups with a possibility of additional substitution, $R_{101}$ to $R_{126}$ may further have a substituent, and the substituent in that case is the same as the substituent listed for the hetero-ring group represented by A.

Dyes represented by the following formulas DS-1 to DS-9 among compounds represented by the general formula (1) are particularly preferable. "A" in the general formulas DS-1 to DS-9 represents a group with the same meaning as that of "A" in the general formula (1).

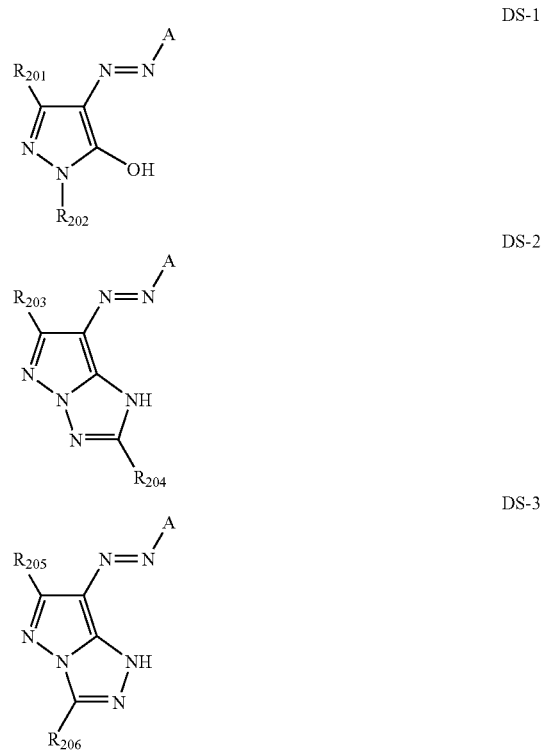

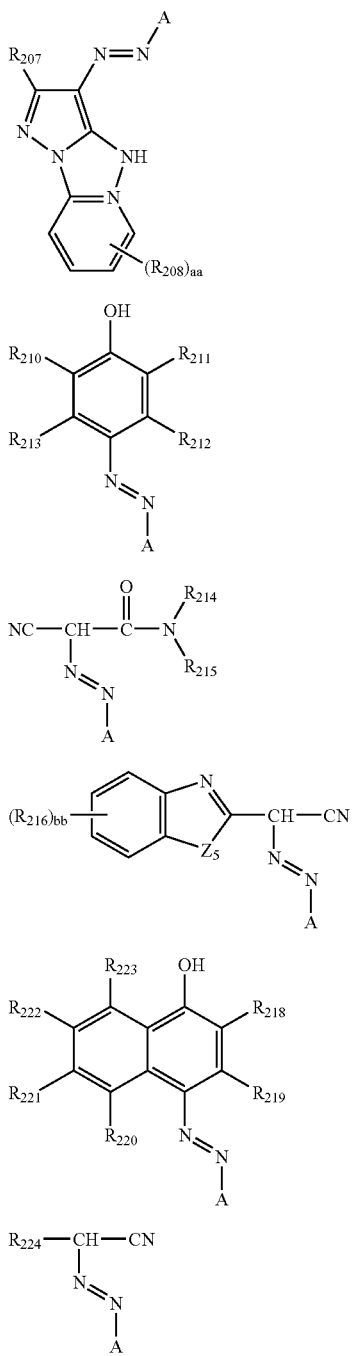

In the formula DS-1, $R_{201}$ represents alkyl group, aryl group, alkoxy group, amino group (including anilino group), alkoxycarbonyl group, cyano group, acylamino group, or carbamoyl group; $R_{202}$ represents hydrogen atom, alkyl group, aryl group, or hetero-ring group. Preferably, $R_{201}$ is alkoxycarbonyl group, cyano group, and carbamoyl group and $R_{202}$ is alkyl group and aryl group.

In the formula DS-2, $R_{203}$ represents hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{204}$ represents alkyl group, aryl group, or hetero-ring group. $R_{203}$ is preferably hydrogen atom and alkyl group, and the alkyl group particularly preferably includes methyl group, ethyl group, isopropyl group, and t-butyl group. $R_{204}$ is most preferably alkyl group.

In the formula DS-3, $R_{205}$ represents hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{206}$ represents alkyl group, aryl group, hetero-ring group, alkylthio group, arylthio group, alkoxycarbonyl group, or carbamoyl group. $R_{205}$ is preferably hydrogen atom and alkyl group, and the alkyl group particularly preferably includes methyl group, ethyl group, isopropyl group, and t-butyl group. $R_{206}$ is preferably alkyl group, aryl group, or alkylthio group, most preferably alkyl group.

In the formula DS-4, $R_{207}$ represents hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{208}$ represents halogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, alkoxycarbonyl group, or carbamoyl group; "aa" represents an integer of 0 to 4. Provided that "aa" is 2 to 4, the $R_{208}$ groups may be the same or different. Preferably, $R_{207}$ is hydrogen atom and alkyl group, and the alkyl group particularly preferably includes methyl group, ethyl group, isopropyl group, and t-butyl group. $R_{208}$ is preferably halogen atom, alkyl group, alkoxy group, acylamino group, and alkylsulfonylamino group.

In the formula DS-5, $R_{210}$ and $R_{211}$ represent hydrogen atom, halogen atom, alkyl group, aryl group, acylamino group, alkoxycarbonyl group, aminocarbonylamino group, alkylsulfonylamino group, arylsulfonylamino group, alkoxycarbonylamino group, or carbamoyl group; $R_{212}$ and $R_{213}$ represent hydrogen atom, halogen atom, alkyl group, alkoxy group, or acylamino group. $R_{210}$ and $R_{211}$ preferably represent hydrogen atom, chlorine atom, bromine atom, alkyl group, and acylamino group, and more preferably at least one of $R_{210}$ and $R_{211}$ is hydrogen atom.

In the formula DS-6, $R_{214}$ and $R_{215}$ independently represent hydrogen atom, alkyl group, aryl group, or hetero-ring group, and one of $R_{214}$ and $R_{215}$ is preferably hydrogen atom.

In the formula DS-7, $R_{216}$ represents halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group; $Z_5$ represents oxygen atom, sulfur atom, or $-N(R_{217})-$, where $R_{217}$ represents hydrogen atom, alkyl group, aryl group, or hetero-ring group. "bb" represents an integer of 1 to 4. Provided that "bb" is 2 to 4, the $R_{216}$ groups may be the same or different. $R_{216}$ is preferably halogen atom, acylamino group, alkylsulfonylamino group, sulfamoyl group, and carbamoyl group. Preferably, $Z_5$ is oxygen atom, sulfur atom, and $-N(R_{217})-$, where $R_{217}$ is alkyl group. More preferably, $Z_5$ is oxygen atom and sulfur atom.

In the formula DS-8, $R_{218}$ represents hydrogen atom, halogen atom, alkyl group, aryl group, acylamino group, alkylsulfonylamino group, arylsulfonylamino group, alkoxycarbonyl group, aminocarbonylamino group, carbamoyl group, or sulfamoyl group; $R_{220}$ and $R_{223}$ represent hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ represent hydrogen atom, chlorine atom, bromine atom, alkyl group, and acylamino group. $R_{218}$ is preferably hydrogen atom, acylamino group, alkylsulfonylamino group, arylsulfonylamino group, alkoxycarbonyl group, aminocarbonylamino group, carbamoyl group, and sulfamoyl group. $R_{220}$ and $R_{223}$ are preferably hydrogen atom, acylamino group, alkoxycarbonylamino group, and alkylsulfonylamino group. $R_{219}$, $R_{221}$, and $R_{222}$ are preferably hydrogen atom.

In the formula DS-9, $R_{224}$ represents alkyl group or aryl group

In the formulas DS-1 to DS-9, preferable carbon numbers and specific examples of the individual groups listed in the descriptions of the groups represented by $R_{201}$ to $R_{224}$ are the same as those listed in the description of the substituent for the hetero-ring group represented by "A".

Provided that $R_{201}$ to $R_{224}$ in the formulas DS-1 to DS-9 are groups with a possibility of additional substitution, $R_{201}$ to $R_{224}$ may have additional substituents. The substituents then are the same as those listed in the description of the substituent for the hetero-ring group represented by "A".

Specific compound examples of the azo dye represented by the general formula (1) in accordance with the invention are described below, but the invention is not limited to these examples.

D-1
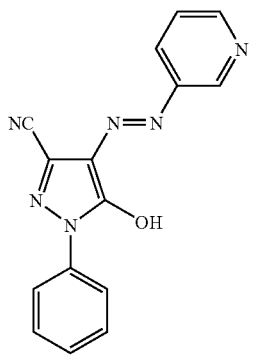

D-2
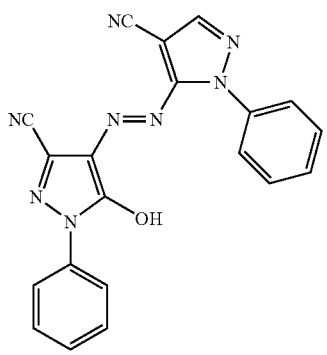

-continued

D-3
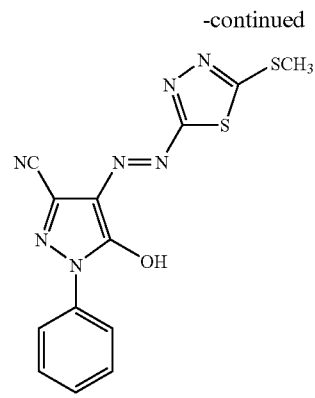

D-4
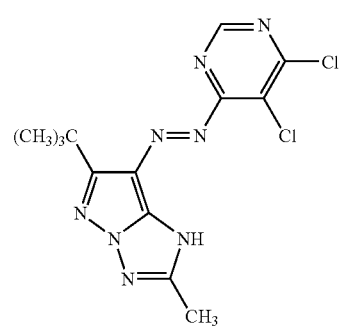

D-5
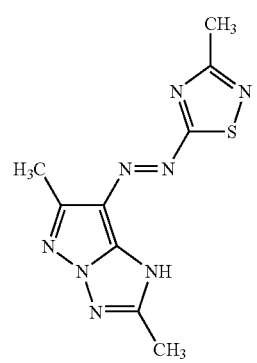

D-6
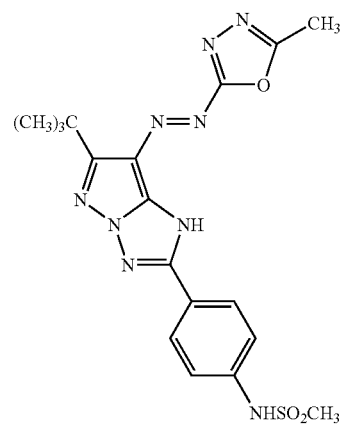

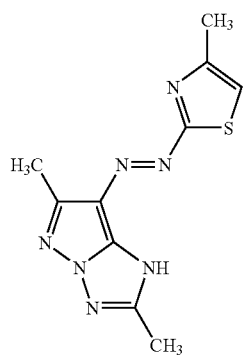
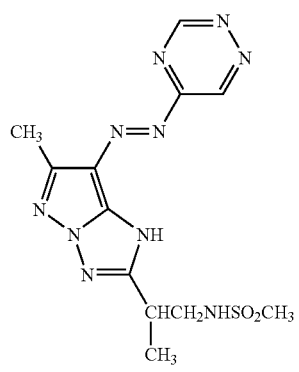
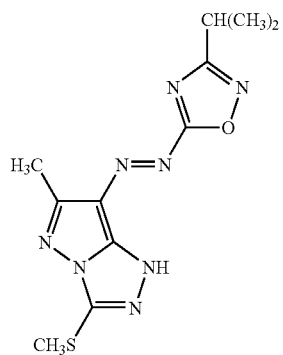
D-7
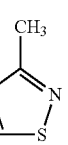
D-8
D-9
D-10
D-11
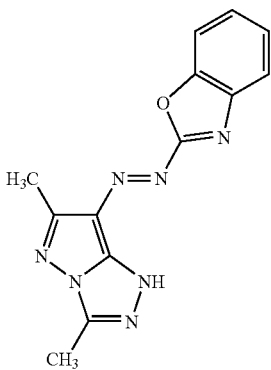
D-12
D-13
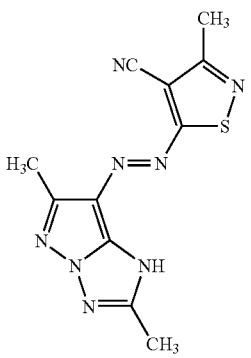
D-14
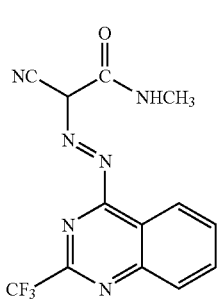

-continued
D-15
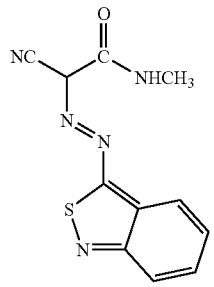
D-16
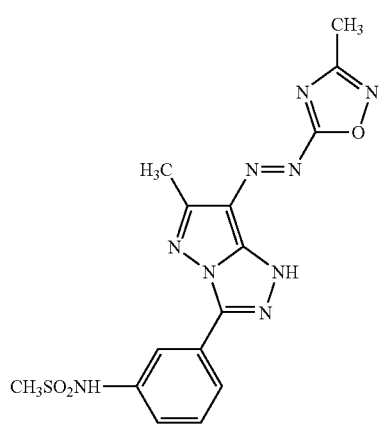
D-17
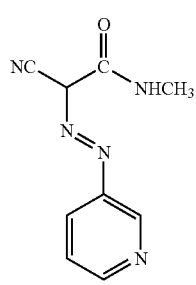
D-18
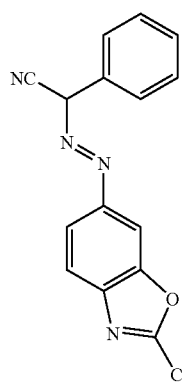
D-19
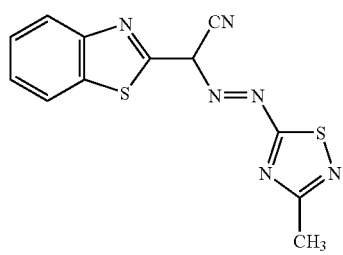
-continued
D-20
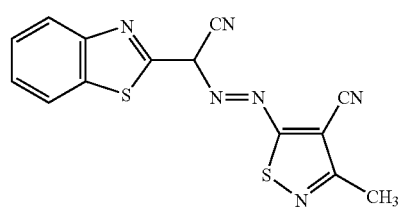
D-21
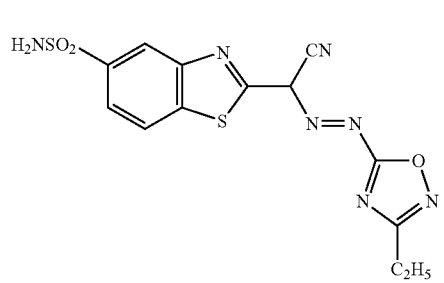
D-22
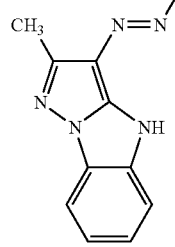
D-23
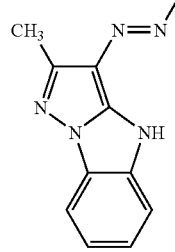

-continued
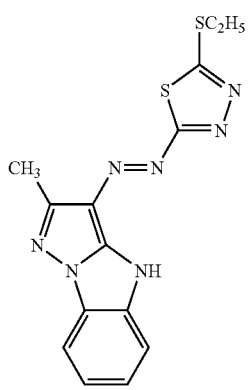
D-24
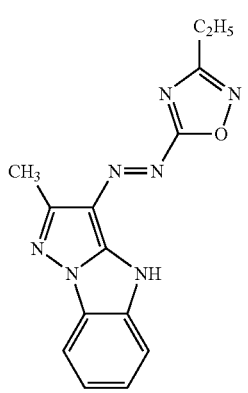
D-25
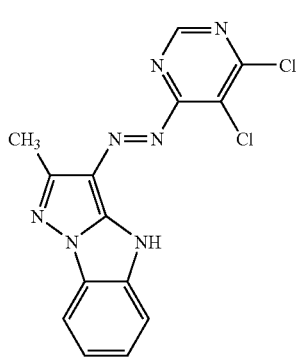
D-26
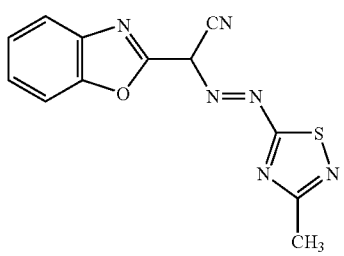
D-27
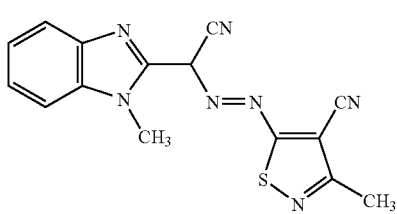
D-28
-continued
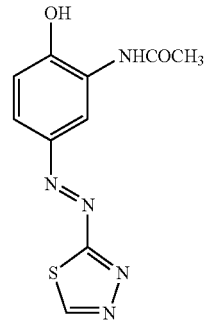
D-29
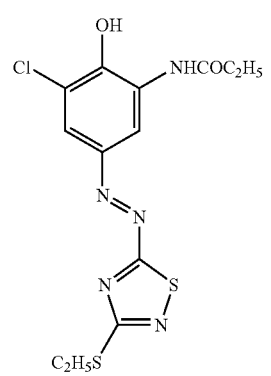
D-30
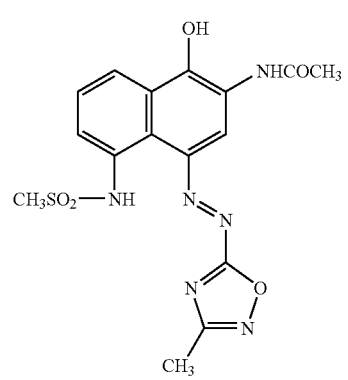
D-31
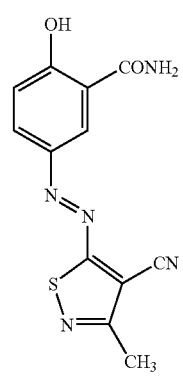
D-32

-continued
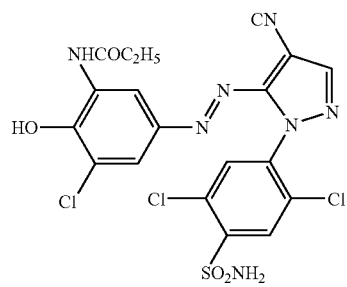
D-33
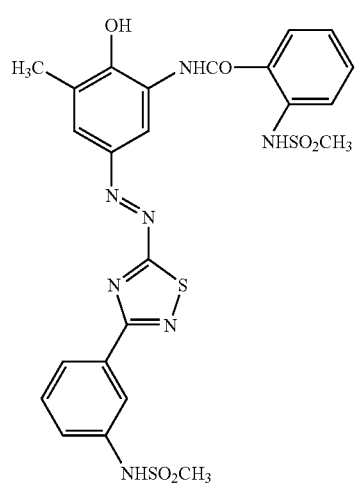
D-34
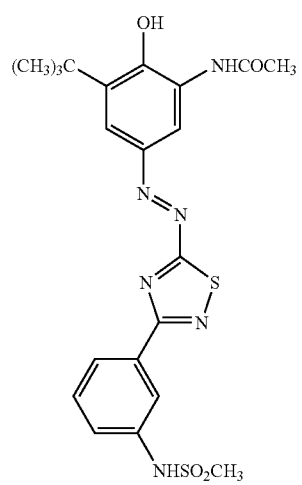
D-35
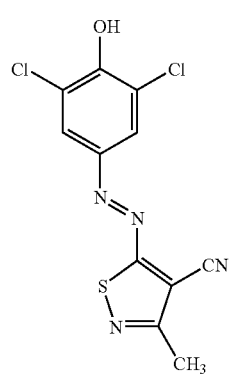
D-36
-continued
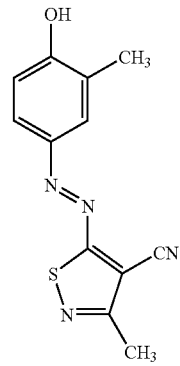
D-37
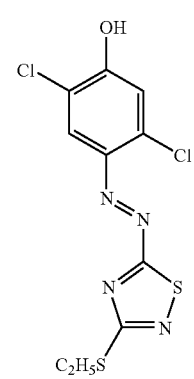
D-38
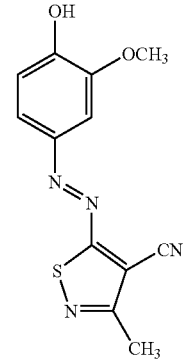
D-39
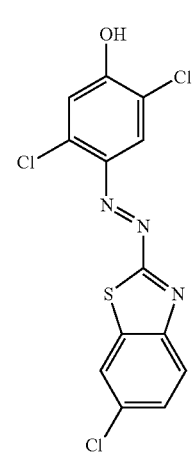
D-40

-continued
D-41 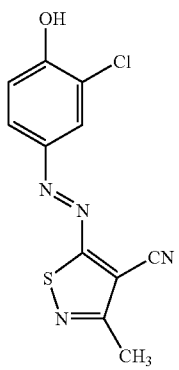
D-42 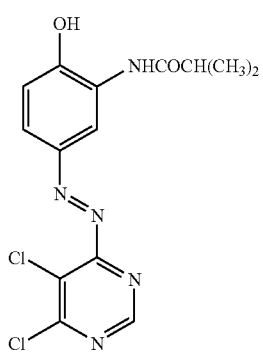
D-43 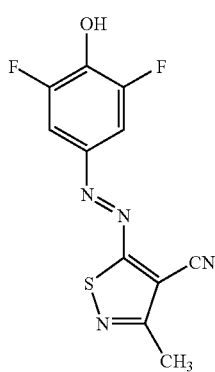
D-44 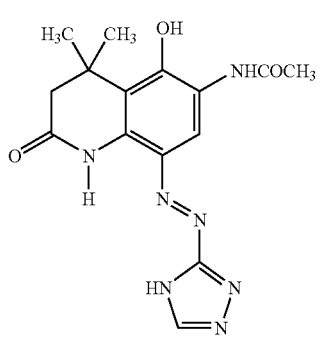
-continued
D-45 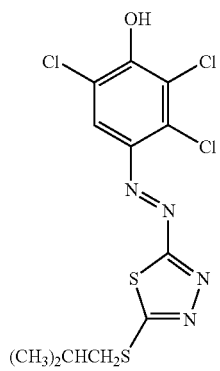
D-46 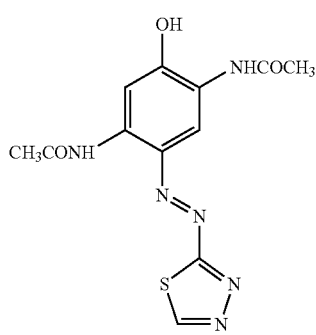
D-47 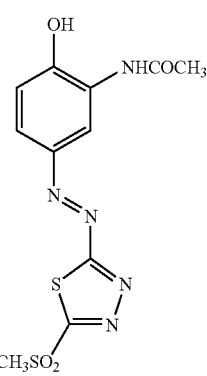
D-48 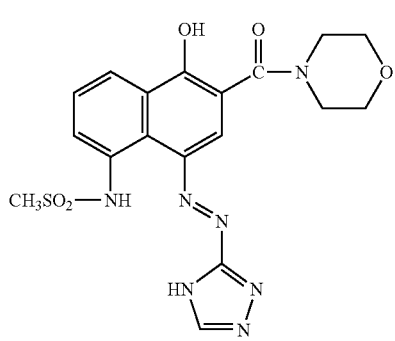

-continued
D-49
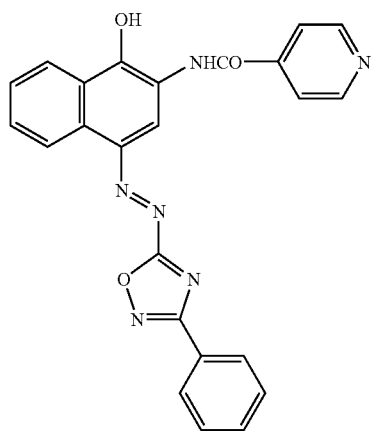
D-50
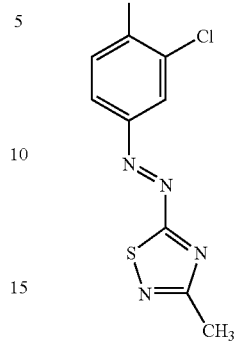
D-51
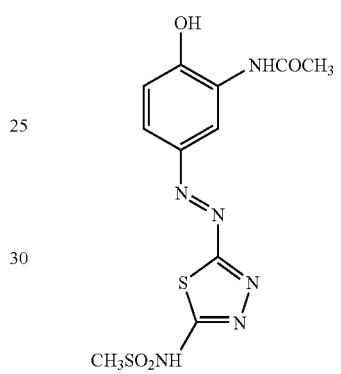
D-52
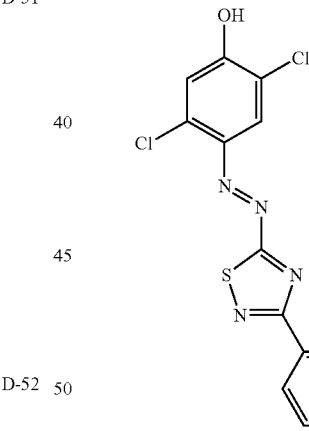
-continued
D-53
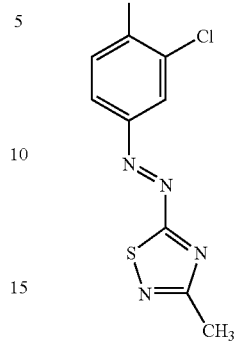
D-54
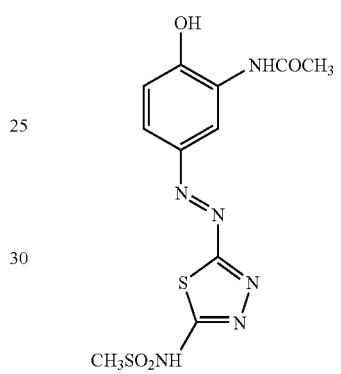
D-55
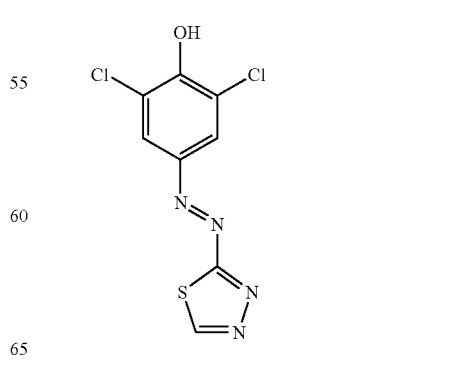
D-56
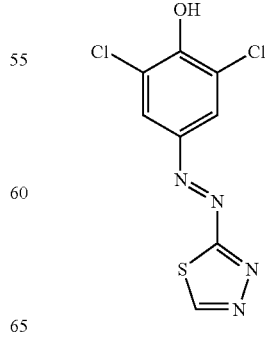

D-57 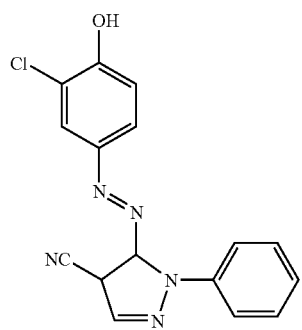
D-58 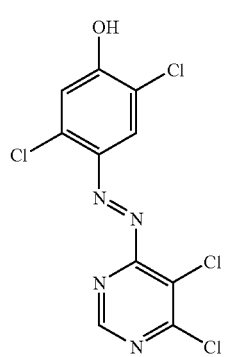
D-59 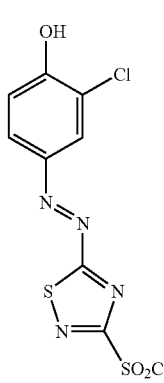
D-60 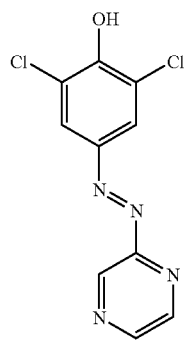
D-61 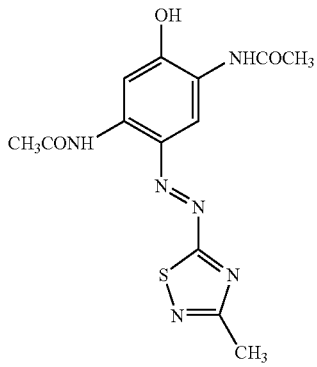
D-62 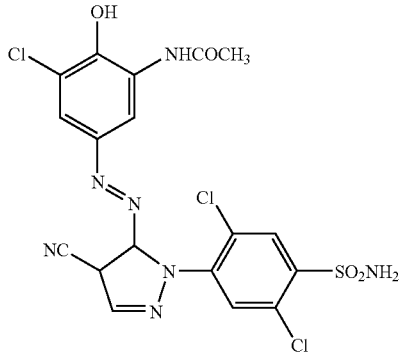
D-63 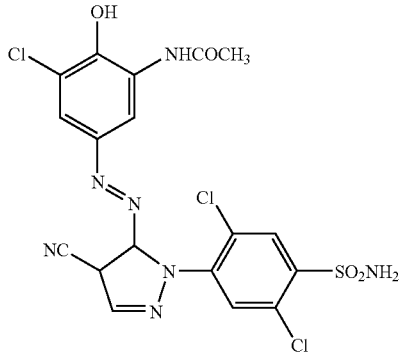
D-64 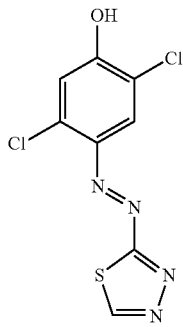

-continued
D-65
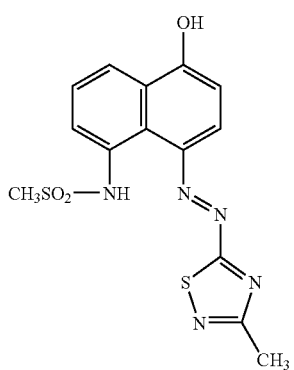
D-66
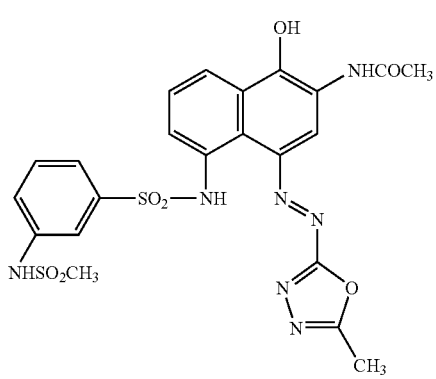
D-67
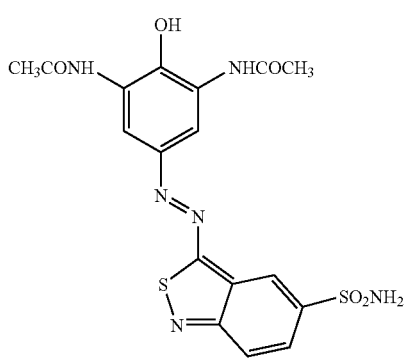
D-68
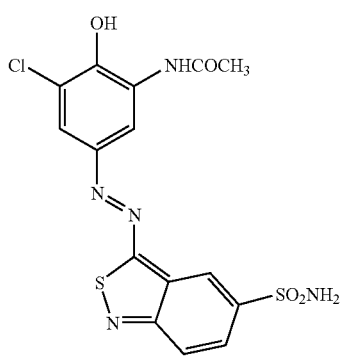
-continued
D-69
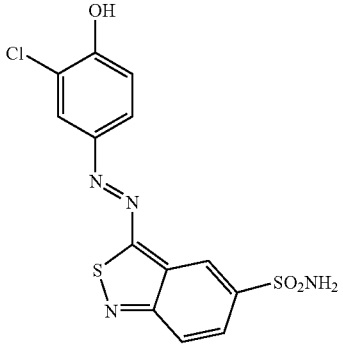
D-70
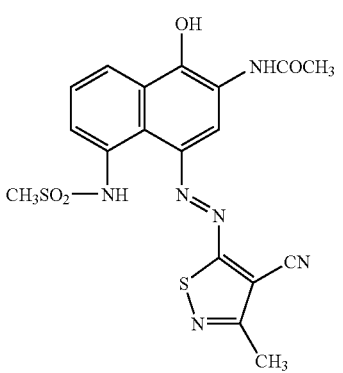
D-71
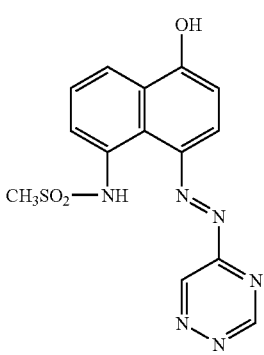
D-72
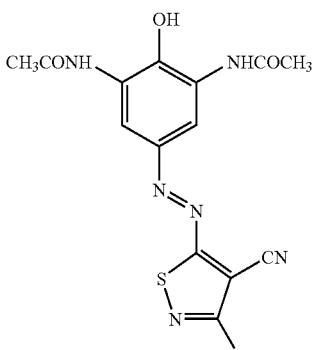

-continued
D-73
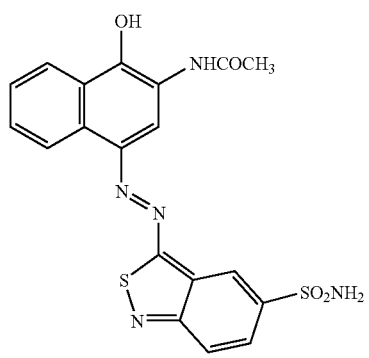
D-74
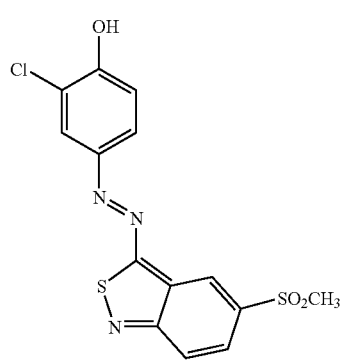
D-75
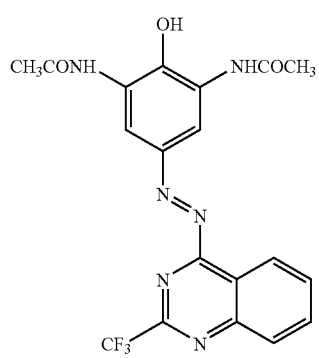
D-76
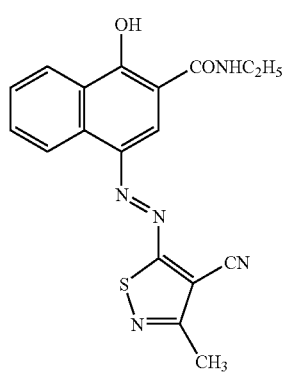
-continued
D-77
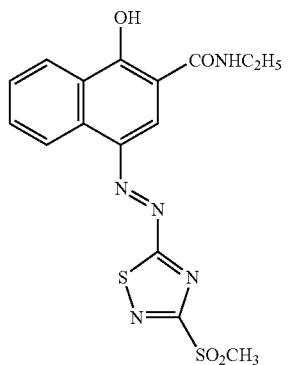
D-78
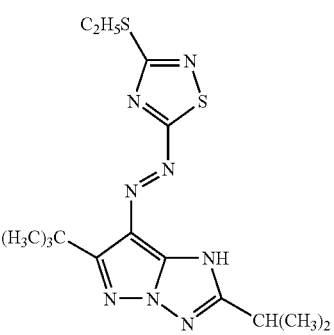
D-79
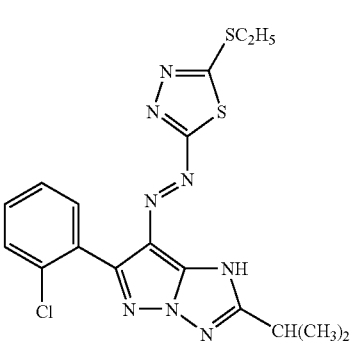
D-80
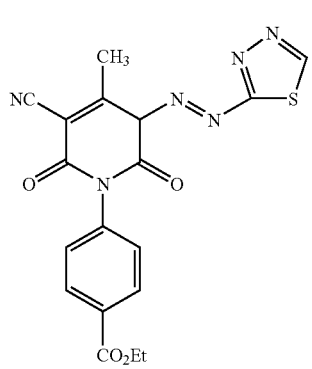

D-81
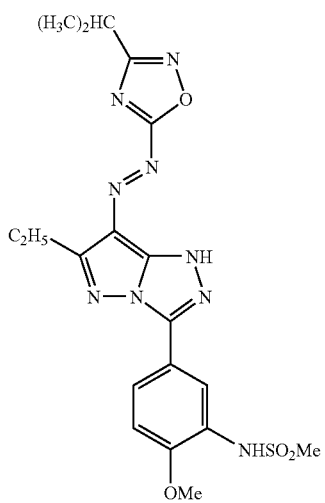
D-82
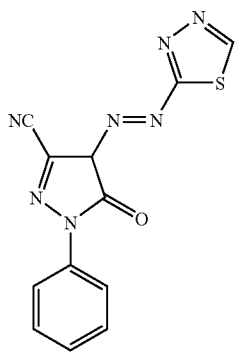
D-83
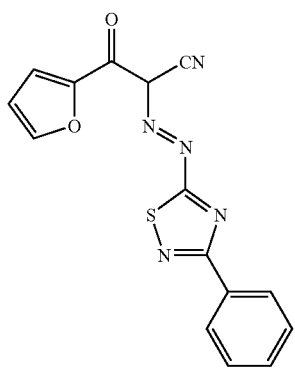
D-84
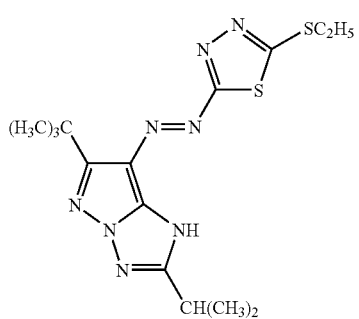
D-85
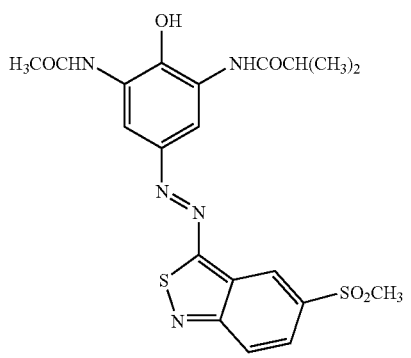
D-86
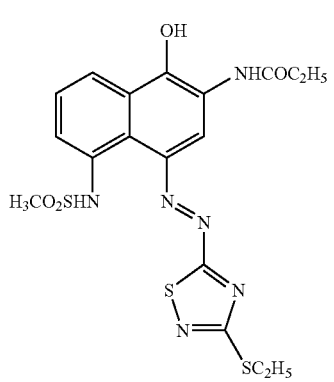
D-87
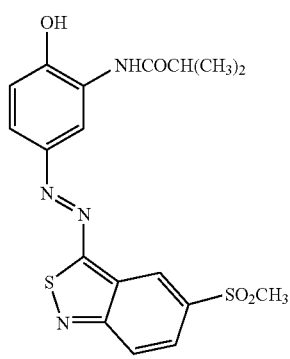
D-88
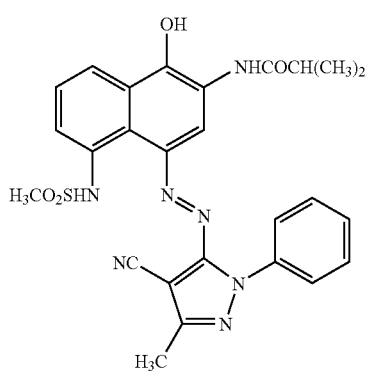

-continued
D-89
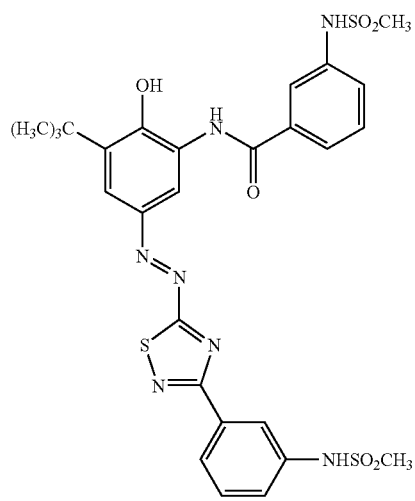
D-90
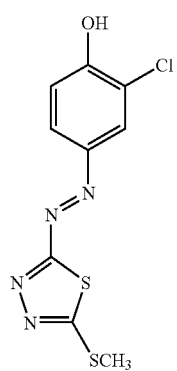
D-91
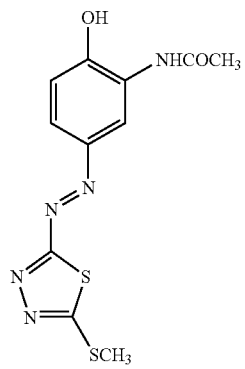
D-92
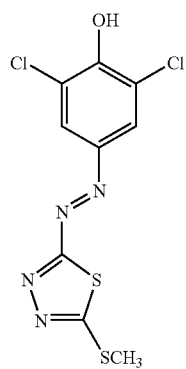
-continued
D-93
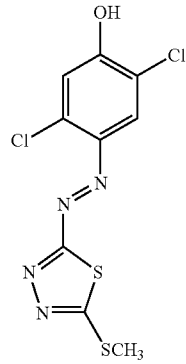
D-94
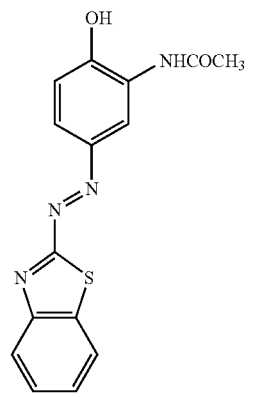
D-95
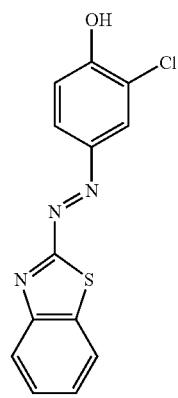
D-96
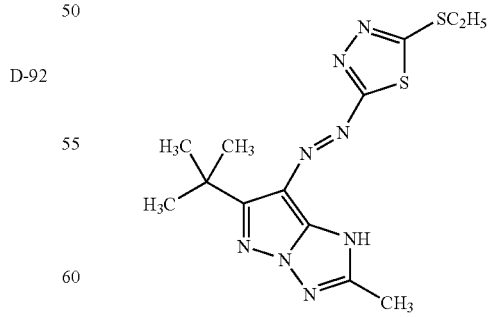

-continued
D-97
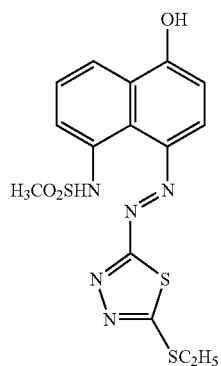
D-98
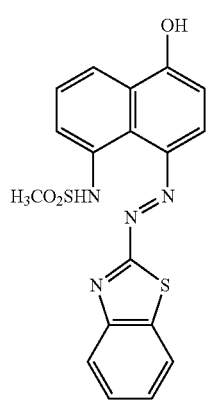
D-99
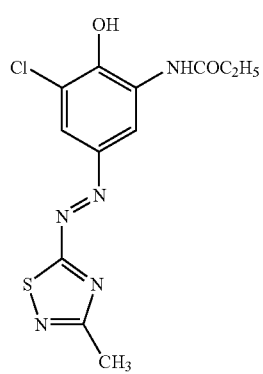
D-100
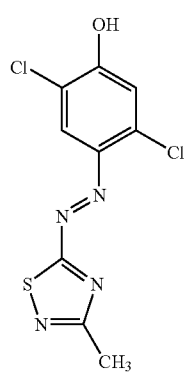
-continued
D-101
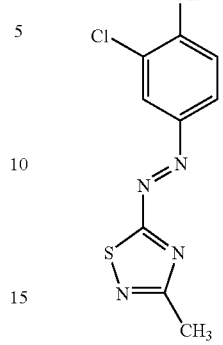
D-102
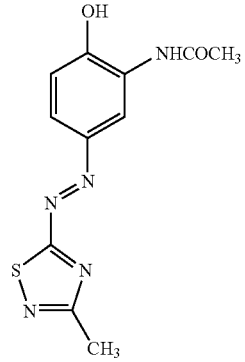
D-103
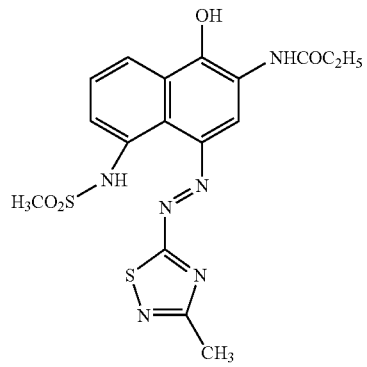
D-104
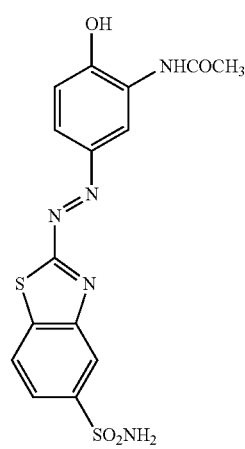

-continued
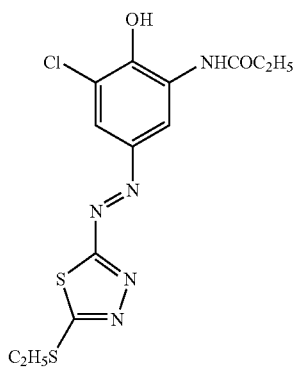
D-105
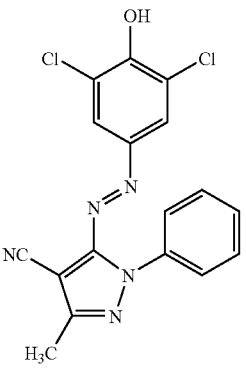
D-109
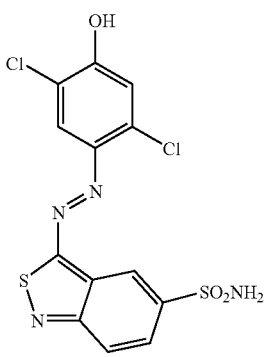
D-106
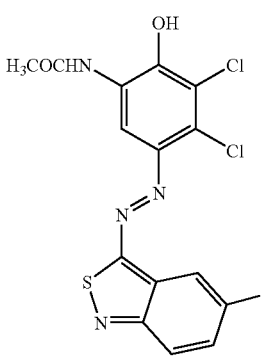
D-110
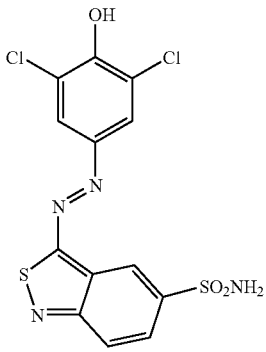
D-107
D-111
D-108
D-112

-continued

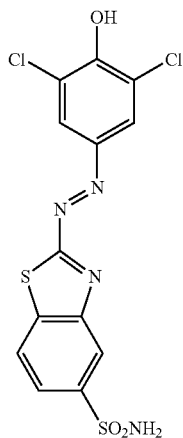
D-113

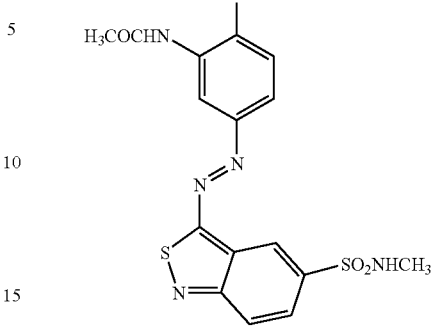
D-117

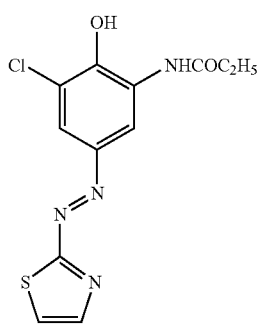
D-114

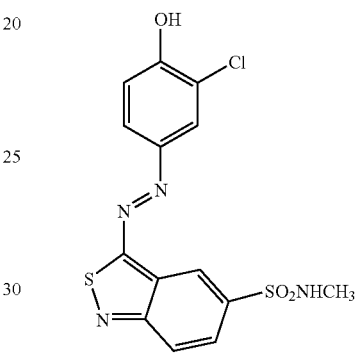
D-118

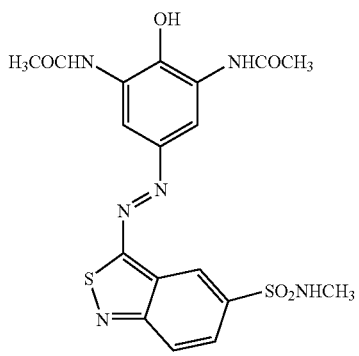
D-115

One or more of the above mentioned, particularly preferred azo direct dyes D-1 to D-118 can be used. Alternatively it may be used in combination with other generally known direct dyes or with oxidative dyes.

Examples of additional direct dyes that can be used in combination with the direct dyes of the invention include, Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 46 (C.I. 110825), Basic Red 76 (C.I. 12245), Basic Red 118 (C.I. 12251:1), Basic Yellow 28 (C.I. 48054) and Basic Yellow 57 (C.I. 12719); cationic dyes as described in Japanese Patent Publication No. Sho 58-2204, Japanese Patent Application Laid-Open (kokai) No. Hei 9-118832, Japanese Language Laid-Open Publications (PCT) Nos. Hei 8-501322 and Hei 8-507545; and methine type cationic dyes having a cyanine structure represented by the below-described formulas.

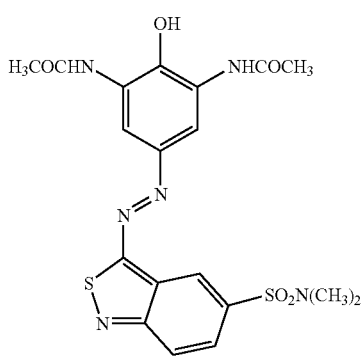
D-116

Yellow dye

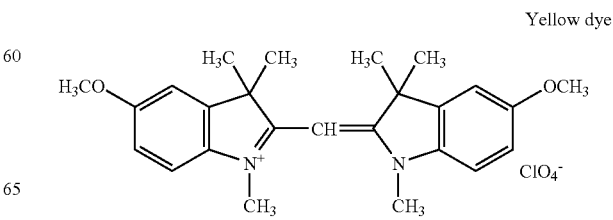

Orange dye

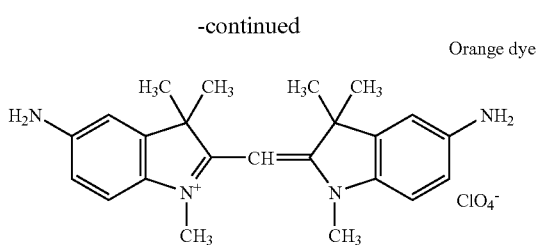

The combined use of the direct dye (1) with one or more oxidative dyes attains a markedly more vivid and stronger colour which is not possible by the use of an oxidation dye alone. For the oxidation dye, known developers and couplers ordinarily employed for an oxidation type hair dye can be used.

Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethylparaphenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

At least one of the above-exemplified ones can be used as the developer and coupler. The amount of each of the developer and coupler is preferably 0.01 to 20 wt. %, especially 0.5 to 10 wt. % each based on the whole composition (after mixing of all the component parts when the composition is a two part or three part composition; this will be applied equally hereinafter).

To the hair dye composition of the present invention, a known autoxidation dye typified by an indole or an indoline, or a known direct dye such as a nitro dye or a disperse dye can also be added.

The azo dyes represented by the formula (1) are preferably added in an amount of 0.0001 to 20 wt. %, more preferably 0.001 to 20 wt. %, further preferably 0.05 to 10 wt. %, especially 0.1 to 5 wt. % based on the whole composition. When another dye is used in combination with the direct dye (1), the total amount of dyes is 0.001 to 20 wt. %, preferably 0.01 to 20 wt. %, more preferably in the range from 0.05 to 10 wt. %, especially 0.1 to 5 wt. %, based on the whole composition.

The pKa of azo dyes represented by the formula (1) is preferably in the range 1.5 to 9, more preferably 2 to 8 and most preferably 2 to 7.5. The pKa of the azo dyes is one possibility for determining the dyeing power of the dyes.

In the hair dye composition of the present invention, the direct dye (1) exhibits high storage stability within a wide pH range from 2 to 11 which is a pH range employed ordinarily for hair dyes, so that the hair dye composition can be used freely in the above-described pH range. Use in a pH range of 5 or greater is however preferred from the viewpoint of dyeing property. Moreover, owing to high stability of the direct dye against an alkali agent, the hair dye composition can be used at a pH above 8, particularly 8 to 11 which permits a high dyeing power, and even after storage for a long period of time, it exhibits high dyeing power without decomposition of the direct dye. Examples of the alkali agent that may be used in the dyeing composition include ammonia, alkanolamines such as monoethanolamine and isopropanolamine or salts thereof, guanidium salts such as guanidine carbonate, hydroxide salts such as sodium hydroxide and sodium, potassium or calcium carbonate and the like carbonates. The alkali agent is preferably added in an amount of 0.01 to 20 wt. %, more preferably 0.1 to 10 wt. %, especially 0.5 to 5 wt. % based on the whole composition.

Since in the hair dye composition of the present invention, the direct dye (1) has high stability against an oxidizing agent, it can be applied to the hair after mixing with an oxidizing agent. In other words, it can be provided in the form composed of a first component part containing alkaline agents and the direct dye (1), optionally together with any other known direct dyes or oxidation dyes and a second component part containing an oxidizing agent. In this case, hair dyeing and bleaching can be carried out simultaneously, which facilitates more vivid hair dyeing. Examples of the oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred for hair bleaching property, stability of the dye and availability. It is also preferred to use a combination of hydrogen peroxide with at least one of the above mentioned other oxidizing agents. The oxidizing agent is preferably added in an amount of 0.5 to 10 wt. %, especially 1 to 8 wt. %, based on the whole composition. The mixing ratio of the first component part containing the direct dye (1) with the oxidizing-agent-containing second component part preferably ranges from 2:1 to 1:3 in terms of a volume ratio.

The hair dye composition of the present invention may comprise from about 0.01% to about 30% by weight of the composition, preferably from about 0.1% to about 20%, more preferably from about 0.1% to about 10% of a conditioning agent suitable for application to the hair. The conditioning agents are typically polymers or oils which are soluble or dispersible in the hair dye compositions, and are deposited on to the hair when rinsed or diluted with water or shampoo.

Suitable conditioning agents for use in the compositions herein are those conditioning agents characterized generally as silicones (e.g. silicone oils, cationic silicones, silicone gums and silicone resins), organic conditioning oils (e.g.

hydrocarbon oils, polyolefins, and fatty esters) or combinations thereof, or those conditioning agents which otherwise form liquid, dispersed particles in the aqueous surfactant.

The conditioning agent of the hair dye compositions of the present invention is preferably an insoluble silicone conditioning agent. The silicone conditioning agent particles may comprise volatile silicone, non-volatile silicone, or combinations thereof. Preferred are non-volatile silicone conditioning agents.

Suitable silicone oils for use herein include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes with the following general formula (2):

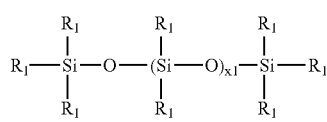
(2)

wherein $R_1$ is aliphatic, preferably alkyl or alkenyl, or aryl, $R_1$ can be substituted or unsubstituted, an x1 is an integer from 1 to about 8,000.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248). Although ethylene oxide or mixtures of ethylene oxide and propylene oxide may also be used, the ethylene oxide and polypropylene oxide concentrations must be sufficiently low to prevent solubility in water and the compositions described herein.

Alkylamino substituted silicones suitable for use herein include, but are not limited to, those of the following general formula (3):

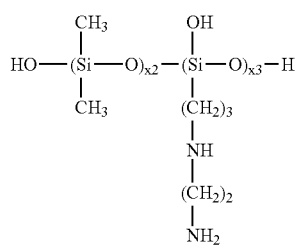
(3)

wherein x2 and x3 are integers. This polymer is also known as "Amodimethicone."

An example of a cationic silicone is the polymer known as "trimethylsilylamodimethicone", which is shown below in formula (4):

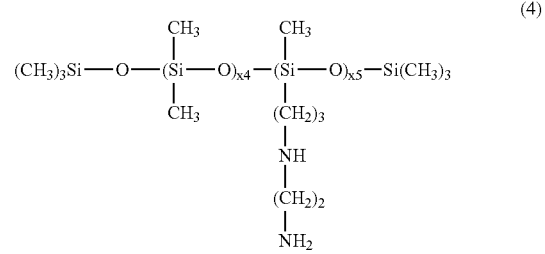
(4)

wherein x4 and x5 are integers.

Other silicone cationic polymers which may be used herein are represented by the general formula (5):

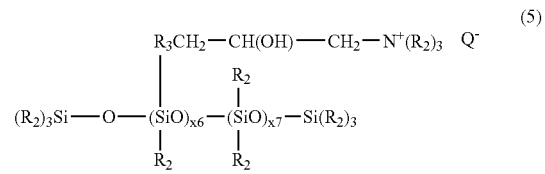
(5)

wherein $R_2$ is a monovalent hydrocarbon radical from $C_1$ to $C_{18}$, preferably an alkyl or alkenyl radical, such as methyl; $R_3$ is a hydrocarbon radical, preferably a $C_1$ to $C_{18}$ alkylene radical or a $C_1$ to $C_{18}$ alkyleneoxy radical, more preferably a $C_1$ to $C_8$ alkyleneoxy radical; $Q^-$ is a halide ion, preferably chloride; x6 is an average statistical value from 2 to 20, preferably from 2 to 8; x7 is an average statistical value from 20 to 200, preferably from 20 to 50.

Other silicone fluids suitable for use herein are the insoluble silicone gums. The silicone gums typically have a weight average molecular weight in excess of about 200,000, preferably from about 200,000 to about 1,000,000. Specific non-limiting examples of silicone gums for use herein include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the scilicone resin.

The conditioning component of the hair dye compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones as described above. The conditioning oils may add shine and luster to the hair. Additionally, they may enhance dry combing and dry hair feel.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from 1 mPa·s to about 200 mPa·s, more preferably from about 1 mPa·s to about 100 mPa·s, most preferably from about 2 mPa·s to about 50 mPa·s.

Suitable organic conditioning oils for use as conditioning agents in the compositions of the present invention include hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably contain from about 12 to about 19 carbon atoms. Branched chain hydrocarbon oils, including hydrocarbon polymers, typically will contain more than 19 carbon atoms.

Organic conditioning oils for use in the compositions of the present invention can also include liquid polyolefins, more preferably liquid poly-α-olefins, most preferably hydrogenated liquid poly-α-olefins. Polyolefins for use herein are prepared by polymerisation of $C_4$ to about $C_{14}$ olefinic monomers, preferably from about $C_6$ to about $C_{12}$.

Other suitable organic conditioning oils for use as the conditioning agent in the compositions of the present include e.g. fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or other linkages, etc.).

Suitable for use in the compositions of the present invention are alkyl and alkenyl esters of fatty acids having aliphatic chains with from about 10 to 22 carbon atoms, and alkyl and alkenyl fatty alcohol carboxylic acid esters having a $C_{10}$ to about C22 alkyl and/or alkenyl alcohol-derived aliphatic chain, and mixtures thereof. Specific examples of preferred fatty esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate, and dioleyl adipate.

The hair dye compositions of the present invention may comprise from about 0.02% to about 5%, by weight of the composition, preferably from about 0.05% to about 3%, more preferably from about 0.1% to about 2%, most preferably from about 0.5% to about 1%, of at least one organic, cationic deposition and conditioning polymer suitable for application to the hair. Additionally, anionic, non-ionic and/or amphoteric polymers may be incorporated, wherein the total amount of the polymers of any type falls within the above range.

Any anionic counterions may be used in association with the cationic polymers so long as the cationic polymers remain soluble in the composition, and so long as the counterions are physically and chemically compatible with the essential components of the hair dye composition or do not otherwise unduly impair product performance, stability or aesthetics. Non-limiting examples of such counterions include: halide ions(e.g., chloride ion, fluoride ion, bromide ion, iodide ion), sulfate ion, methylsulfate ion, and mixtures thereof. Examples of cationic polymers which may be suitably employed in the hair dye compositions herein include, but are not limited to cationic polysaccharides (e.g. cationic cellulose derivatives and cationic guars), copolymers of vinyl monomers, vinyl pyrrolidone copolymers, cationic modified proteins, and certain polymeric quaternary salts. Such cationic polymers are described in detail below.

Preferred cationic polymers for use in the hair dye compositions of the present invention are those known as cationic polysaccharides. Cationic polysaccharides are those polymers based on $C_5$ to $C_6$ sugars and derivatives which have been made cationic by engrafting of cationic moieties on the polysaccharide backbone, and include homopolymers, copolymers, terpolymers, and so forth, of quaternary ammonium or cationic amine-substituted monomer units, optionally in combination with non-cationic monomers. The polysaccharides may be composed of one type of sugar or of more than one type. The cationic amines can be primary, secondary, or tertiary amines (preferably secondary or tertiary), depending upon the particular species and the selected pH of the hair dye composition. The monomers may be in straight chain or branched chain geometric arrangements. All of the monomer units may have cationic nitrogen-containing moieties attached thereto, preferably some of the monomer units do not have such moieties attached.

Cationic polysaccharide polymers include the following: cationic celluloses, cationic starches and so on.

Suitable polysaccharide cationic polymers for use in the hair dye compositions of the present invention are the cationic cellulose derivatives and cationic starch derivatives. Such cationic polymers include those which conform to the general formula (6):

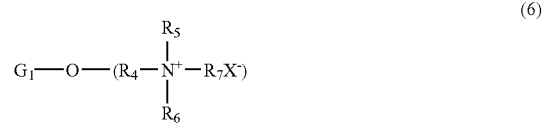

(6)

wherein $G_1$ is an anhydroglucose residual group (e.g. a starch or cellulose anhydroglucose residue); $R_4$ is an alkylene oxyalkylene, polyoxyalkylene, or hydroxyalkylene group, or a combination thereof; $R_5$, $R_6$ and $R_7$ are independently alkyl, aryl, alkylaryl, arylalkyl, alkoxyalkyl, or alkoxyaryl groups, each group containing up to about 18 carbon atoms, and the total number of carbon atoms for each cationic moiety (i.e. the sum of carbon atoms in $R_5$, $R_6$ and $R_7$) preferably being about 20 or less; and $X^{31}$ is an anionic counterion.

Preferred cationic polymers include, but are not limited to, those polymers available from Amerchol Corporation, in their Polymer JR and LR series of polymers, and salts of hydroxyethyl cellulose reacted with trimethyl ammonium substituted epoxide, known in the industry (CTFA) as Polyquaternium 10 (e.g. JR 30M®, available from Amerchol Corporation). Preferred Polyquaternium 10 polymers for use herein, typically have a charge density from about 0.3 meq/g to about 3 meq/g and a molecular weight from about 200,000 to about 1,500,000. Another non-limiting example of a preferred type of cationic cellulose includes the polymeric quaternary ammonium salt of hydroxyethyl cellulose reacted with lauryl dimethyl ammonium-substituted epoxide, known in the industry (CTFA) as Polyquaternium 24, (e.g. Polymer LM 200®, available from Amerchol Corporation).

Other suitable polysaccharide cationic polymers for use in the hair dye compositions of the present invention are cationic guar polymers. Guars are cationically substituted galactomannan (guar) gum derivatives. The molecular weight of such derivatives ranges typically from about 50,000 to about 2,500,000, preferably from about 50,000 to about 1,000,000, more preferably from about 50,000 to about 700,000.

Guar gum for use in preparing these guar gum derivatives is typically obtained as a naturally occurring material from the seeds of the guar plant. The guar molecule itself is a straight chain mannan branched at regular intervals with single membered galactose units on alternative mannose units. The mannose units are linked to each other by means of β (1-4) glycosidic linkages. The galactose branching arises by way of an α (1-6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the preferred cationic charge density described above.

The cationic guar polymer is exemplified by guar hydroxypropyltrimehtylammonium chloride, represented by the general formula (7), wherein $G_2$ is guar gum:

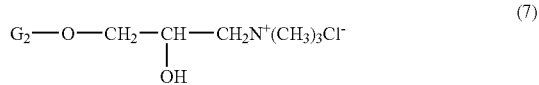

(7)

Other suitable cationic polymers for use in the hair dye compositions of the present invention are copolymers of vinyl monomers, having cationic protonated amine or quaternary ammonium functionalities, reacted with water soluble monomers. Examples of such monomers include: acrylamide, methacrylamide, alkyl and dialkyl acrylamides, alkyl and dialkyl methacrylamides, alkyl acrylate, alkyl methacrylate, vinyl caprolactone, vinyl pyrrolidone, and mixtures thereof. The alkyl and dialkyl substituted monomers preferably have from $C_1$ to $C_7$ alkyl groups, more preferably from $C_1$ to $C_3$ alkyl groups. Other suitable monomers include vinyl esters, vinyl alcohol (made by hydrolysis of polyvinyl acetate), maleic anhydride, propylene glycol, ethylene glycol, and mixtures thereof.

Suitable cationic protonated amino and quaternary ammonium monomers, for inclusion in the cationic polymers of the hair dye composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts; and vinyl quaternary ammonium monomers having cyclic cationic nitrogen-containing rings such as pyridinium, imidazolium, and quaternized pyrrolidones, such as alkyl vinyl imidazolium, alkyl vinyl pyridinium, and alkyl vinyl pyrrolidone salts. The alkyl portions of these monomers are preferably lower alkyl such as the $C_1$–$C_3$ alkyls.

Suitable amine-substituted vinyl monomers for use herein include, dialkylaminoalkyl acrylamide, and dialkylaminoalkyl methacrylamide, wherein the alkyl groups are preferably $C_1$ to $C_7$ hydrocarbyls, more preferably $C_1$ to $C_3$ alkyls.

Other suitable cationic polymers for use in the hair dye compositions of the present invention include: copolymers of 1-vinyl-2-pyrrolidone and 1-vinyl-3-methylimidazolium salt (e.g., chloride salt), known in the industry (CTFA) as Polyquaternium 16 (e.g. Luviquat® FC 370, available from BASF Wyandotte Corporation); copolymers of 1-vinyl-2-pyrrolidone and dimethylaminoethyl methacrylate, known in the industry (CTFA) as Polyquaternium 11 (e.g. Gafquat® 755N, available from ISP Corporation); cationic diallyl quaternary ammonium-containing polymers, including, for example, dimethyldiallyl-ammonium chloride homopolymer, known in the industry (CTFA) as Polyquaternium 6; copolymers of acrylamide and dimethyldiallylammonium chloride, known in the industry (CTFA) as Polyquaternium 7; and mineral acid salts of aminoalkyl esters of homopolymers and copolymers of unsaturated $C_3$ to $C_5$ carboxylic acids.

Still other cationic polymers for use in the hair dye compositions of the present invention are cationic modified proteins, such as lauryldimonium hydroxypropyl collagen (e.g. Croquat® L, available from Croda Corporation) or cocodimonium hydroxypropyl hydrolysed hair keratin (e.g. Croquat®. HH, available from Croda Corporation). Other cationic polymers include the polymeric quaternary salt prepared by the reaction of adipic acid and dimethylaminopropylamine, reacted with dichloroethyl ether, known in the industry (CTFA) as Polyquaternium 2 (e.g. Mirapol® AD-1, available from Rhodia), and the polymeric quaternary salt prepared by the reaction of azelaic acid and dimethylaminopropylether, known in the industry (CTFA) as Polyquaternium 18 (e.g. Mirapol® AZ-1, available from Rhodia Corporation).

The hair dye compositions of the present invention may further comprise from about 0.005% to about 1.5% by weight of the composition, preferably from about 0.025% to about 1.2%, more preferably from about 0.05% to about 1%, more preferably from about 0.1% to about 0.5% of selected polyalkylene glycols suitable for application to the hair. Such poylalkylene glycols should be physically and chemically compatible with the essential components described herein, and should not otherwise unduly impair product stability, aesthetics, or performances.

The polyalkylene glycols suitable for use in the hair dye compositions herein are characterized by the general formula (8):

(8)

wherein $R_8$ is hydrogen, methyl, or mixtures thereof, preferably hydrogen, and n is an integer having an average value from about 1,500 to about 120,000, preferably from about 1,500 to about 50,000, more preferably from about 2,500 to about 25,000, and most preferably from about 3,500 to about 15,000. When $R_8$ is hydrogen, these materials are polymers of ethylene oxide, which are also known as polyethylene glycols. When $R_8$ is methyl, these materials are polymers of propylene oxide, which are also known as polypropylene glycols. When $R_8$ is methyl, it is also understood that various positional isomers of the resulting polymers can exist. Preferred for use herein are polyethylene glycols, poylpropylene glycols, and mixtures thereof.

Specific non-limiting examples of polyethylene glycol polymers for use in the stable alkaline hair dye compositions of the present invention include: PEG 2M, wherein $R_8$ is hydrogen and n has an average value of about 2,000 (e.g. Polyvox WSR® N-10, available from Union Carbide); PEG 5M, wherein $R_8$ is hydrogen and n has an average value of about 5,000 (e.g. Polyvox WSR® N-35 and Polyvox WSR® N-80, both available from Union Carbide); PEG 7M, wherein $R_8$ is hydrogen and n has an average value of about 7,000 (e.g. Polyvox WSR® N-750, available from Union Carbide); PEG 9M, wherein $R_8$ is hydrogen and n has an average value of about 9,000 (e.g. Polyvox WSR® N-3333, available from Union Carbide); PEG 14 M, wherein $R_8$ is hydrogen and n has an average value of about 14,000 (e.g.

Polyvox WSR® N-3000, available from Union Carbide); PEG 23M, wherein $R_8$ is hydrogen and n has an average value of about 23,000 (e.g. Polyvox WSR® N-12k, available from Union Carbide); PEG 90M, wherein $R_8$ is hydrogen and n has an average value of about 90,000 (e.g. Polyvox WSR® 301, available from Union Carbide); and PEG 100M, wherein R is hydrogen and n has an average value of about 100,000 (e.g. Carbowax PEG 4600®, available from Union Carbide). Preferred polyethylene glycols include PEG 7M, PEG 14M, PEG 25M, PEG 90M, and mixtures thereof.

The hair dye compositions of the invention may contain as a further optional component a chelating agent. Chelating agents components are understood to act to sequester (chelate or scavenge) heavy metal ions. These components may also have calcium and magnesium chelation capacity, but preferably they show slectivity to binding heavy metal ions such as iron, manganese and copper. Such chelating agents are valuable in hair dye compositions as herein described for the delivery of controlled oxidising action as well as for the provision of good storage stability of the hair coloring products.

Chelating agents are generally present at a level of from about 0.005% to about 20%, preferably from about 0.01% to about 10%, more preferably from about 0.05% to about 2% by weight of the compositions.

Various chelating agents, including the amino phosphonates, available as Dequest® from Monsanto, the nitriloacetates, the hydroxyethyl-ethylene triamines and the like are known for such use.

Preferred among the above species are diethylene triamine penta (methylene phosphonate), ethylene diamine tri(methylene phosphonate), hexamethylene diamine tetra (methylene phosphonate) and hydroxy-ethylene-1,1 diphosphonate.

The heavy metal ions sequestering agents may be used in the form of their alkali or alkaline earth metal salts.

The hair dye composition of the present invention can also contain surface-active substances. An anionic, non-ionic, cationic, amphoteric or zwitter-ionic surfactant can be incorporated in the hair dye composition of the present invention, and the above described surfactants are compatible if used together.

Examples of anionic surfactants include sulfate-, sulfonate-, carboxylate- and alkyl phosphate-type surfactants, which are usually used in the shampoos.

For example, the well known $C_{10-18}$ alkyl sulfates and in particular the appropriate ether sulfates, for example $C_{12-14}$ alkylether sulfate, laurylether sulfate, in particular with 1 to 4 ethyleneoxide groups in the molecule can be listed as the sulfate-type anionic surfactant. Furthermore, monoglyceride (ether)sulfate, fatty acid amide sulfates which are produced by ethoxylation and following sulfate introduction to the corresponding fatty acid alkanolamide, and their alkali salts as well as salts of long-chained mono and dialkyl phosphates, which represent mild detergent and which can be applied on the hair, also can be used.

Examples of suitable anionic surfactants include alpha-olefinsulfonate or its salts and, in particular, alkali salts of sulfosuccinic acid half-ester, for example disodium salt of the monooctylsulfo succinate and alkali salts of long-chained monoalkylethoxysulfo succinate.

Examples of the suitable carboxylate type surfactants include alkylpolyethercarboxylic acid or their salts and alkamidopolyethercarboxylic acid or their salts.

Such products are well known and have been on the market for a long time, for example under the trade name "AKYPO®" and "AKYPO-SOFT®".

Also $C_{8-20}$ acyl isethionate and likewise sulfofatty acid and their esters can be used, however, in the mixture with other surfactants.

Also mixtures of several anionic surfactants, for example mixtures of an alpha-olefin sulfate and a sulfo succinate, preferably in the relation of 1:3 to 3:1, or an ether sulfate and a polyethercarboxylic acid or an alkylamidoethercarboxylic acid can be used.

The concentration of anionic surfactant is preferably between 0.5 and 10 wt %, in particular between 1 and 5 wt %.

Other examples of suitable non-ionic surfactants are e.g. alkylpolyglucosides, sorbitan esters such as polyethyleneglycol-sorbitan stearate, fatty acid polyglycol ester or also ester of fatty acid and mixed-polymerized polyglycol from ethylene oxide and propylene oxide, as they are on the market, for example, under the trade name "Pluronics®".

Further additionally applicable surfactant is amine oxide. Such amine oxides belong to the state of the art for a long time, for example $C_{12-18}$ alkyldimethylamine oxide such as lauryldimethylamine oxide, $C_{12-18}$ alkylamidopropylamide oxide or alkylamidoethylamine oxides, $C_{12-18}$ alkyldi(hydroxyethyl) amine oxide or alkyldi(hydroxypropyl) amine oxide or also amine oxides which have groups of ethylene oxides and/or propylene oxides in their alkyl chain. Suitable amine oxides are on the market, for example under the trade name of "Ammonyx®", "Aromox®" or "Genaminox®".

Further optical surfactant constituents are fatty acid-mono and dialkanolamide, like coco fatty acid-monoethanolamide and myristic acid-monoisopropanolamide.

Examples of suitable amphoteric or zwitter-ionic surfactants include, in particular, well known betaines such as fatty acid-amidoalkylbetaine and sulfobetaine, for example laurylhydroxysulfobetaine; long-chained alkylamino acids such as cocoaminoacetate, cocoaminopropionate, sodium cocoamphopropionate and sodium cocoamphoacetate are listed as suitable examples.

Examples of suitable cationic surfactants include long-chained quaternized ammonium compounds, which can be used alone or in combination, like cetyltrimethylammonium chloride, dimethylstearylammonium chloride, trimethylacetylammonium bromide, stearyltrimethylammonium chloride, dimethylstearylbenyzlammonium chloride, bnezyltetradecyldimethylammonium chloride, dimethyl di-hydrogenated-tallow ammonium chloride, lauryldimethylbenzylammonium chloride, behenyltrimethylammonium chloride, lauryltrimethylammonium chloride, tris-(oligooxy-ethyl)alkylammonium phosphate, cetylpridinium chloride, etc.

The composition of the present invention can comprise also further preservative agents such as oils and fats. Such are, for example, sun flower oil, almond oil, peach kernel oil, wheat germ oil, macadamia nut oil, night Evening Primrose oil, jojoba oil, castor oil, or also olive or soybean oil, lanolin and its derivatives, likewise mineral oils such as paraffin oil and Vaseline® and a mixture thereof.

If the composition of the present invention is present in the form of an emulsion, the compositions may comprise generally used emulsifying agents. The composition according to the present invention can comprise long-chained fatty acids. As fatty acids, $C_{10-24}$, particularly $C_{12-22}$ fatty acids are preferable, and they can be incorporated in an amount of 0.5 to 15 wt % in particular 1 to 10 wt %, calculated on the whole composition. Behenic acid and stearic acid are particularly suitable, however, other fatty acids for example myristic aicd, palmitic acid, oleic acid or also mixtures of natural or synthetic fatty acids such as coco-fatty acid also can be incorporated.

The hair dye compositions of the present invention may additionally include a thickener at a level of from about 0.05% to about 20%, preferably from about 0.1% to about 10%, more preferably from about 0.5% to about 5% by weight of the composition. Thickening agents suitable for use in the compositions herein are selected from oleic acid, cetyl acohol, oleyl alcohol, sodium chloride, cetearyl alcohol, stearyl alcohol.

Water is the preferred diluent for the compositions according to the present invention. However, the compositions according to the present invention may also include one or more solvents as additional materials. Generally, solvents suitable for use in the dye compositions of the present invention are selected to be miscible with water and are not detrimental to the hair and/or scalp. Solvents suitable for use as additional diluents herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, n-pentanol, propylene glycol, ethylene glycol monoethyl ether, 1,2-hexanediol, butoxyethanol, phenoxyethanol, benzyl alcohol, propylene carbonate and mixtures thereof. Further preferred solvents for the composition of the present invention are 1,2- and 1,3-propanediol, 1-methoxy-2-propanol, 1-ethoxy-2-propanol, 1,3- and 1,4-butanediol, diethylene glycol and its monomethyl and monoethyl ether as well as dipropyleneglycol and its monomethyl and monoethyl ether. The proportion of these diols is preferably between 0.5 and 30 wt %, more preferably 1 to 15 wt %, in particular 5 to 10 wt % of the whole composition. In addition to these $C_{3-6}$ alkanediols or their ethers, also monoalcohols such as ethanol, 1-propanol and 2-propanol; polyalcohols such as glycerine and hexanetriol; ethylcarbitol; benzyl alcohol; benzyloxyethanol; propylene carbonate (4-methyl-1,3-dioxan-2-on); n-alkylpyrrolidone; and urea are also suitable and can be used.

Water is the preferred principal diluent in the compositions according to the present invention. Principal diluent, as defined herein, means, that the level of that diluent present is higher than the total level of any other diluents.

The solvent is present at a level preferably of from about 0.01% to about 99%, preferably from about 0.05 to about 50, more preferably at least from about 0.1% to 15%, most preferably 0.2% to 5% based on the whole composition.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) may be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 1,000 to 100,000 mPa·s, in particular 5,000 to 50,000 mPa s, above all 10,000 to 40,000 mPa s in the stage of application to the hair (after mixing of all the component parts when the composition is a two-part or three-part type). The viscosity is measured at 20° C. by using a Brookfield rotary viscosimeter with a spindle No. 5 at 5 rpm.

The azo dye (1) of the present invention may be used for dyeing human or animal hair. Such hair dyeing method comprises applying the azo dye (1) to the hair, rinsing the hair after completion of the dyeing, and drying the hair after the rinsing.

EXAMPLES

The present invention will be described in greater detail by referring to the examples and comparative examples.

Specific synthetic examples of the compound represented by the general formula (1) in accordance with the invention will be described below.

Synthesis of Listed Compound D-38

The compound was synthetically prepared according to the following scheme.

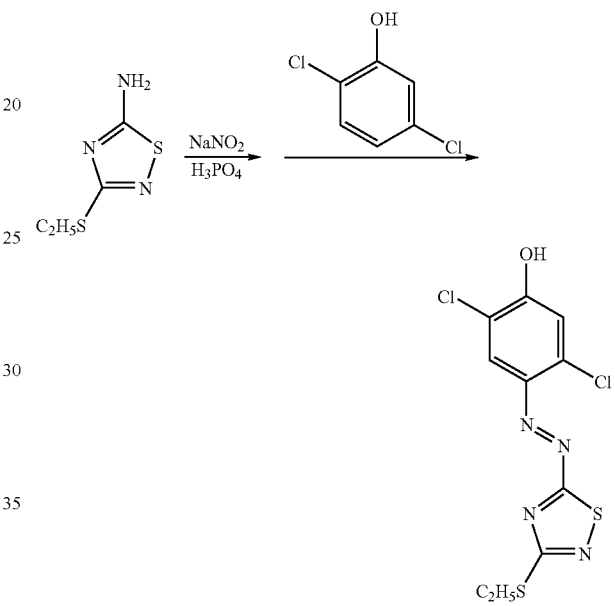

5-Amino-3-ethylthio-1,2,4-thiadiazole (1.93 g; 12.0 mmol) was added to phosphoric acid (50 ml), and the resulting mixture was agitated under cooling in ice water. Sodium nitrite (1.0 g) in crystal form was added to the mixture, which was agitated for one hour. 2,5-Dichlorophenol (1.63 g; 10.0 mmol) was added to methanol (60 ml), and the resulting mixture was agitated under cooling in ice water, to which was then gradually added the diazo solution prepared above. After agitation under cooling for one hour and agitation at room temperature for another hour, water (150 ml) and ethyl acetate (80 ml) were added to the reaction mixture, for extraction. Then, the organic layer was rinsed twice in aqueous saturated saline (60 ml). The organic layer was concentrated under reduced pressure and was purified by silica gel column chromatography, to recover the listed compound D-38 in an amount of 1.88 g (yield of 56%).

Synthesis of Listed Compound D-29

Synthetically prepared according to the following scheme.

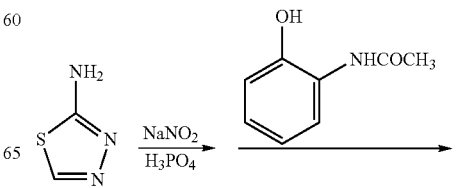

-continued

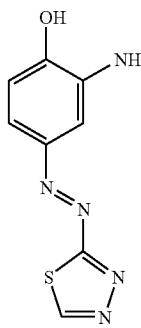

2-Amino-1,3,4-thiadiazole (4.30 g; 42.5 mmol) was added to phosphoric acid (120 ml), and the resulting mixture was agitated under cooling in ice water. Sodium nitrite (2.84 g; 41.1 mmol) in crystal form was added to the mixture, which was agitated for 1.5 hours. 2-Acetylaminophenol (4.70 g; 31.1 mmol) was added to methanol (60 ml), and the resulting mixture was agitated under cooling in ice water, to which was then gradually added the diazo solution prepared above in a divided manner over 2 hours. After agitation under cooling for one hour and agitation at room temperature for another hour, water (240 ml) was added to the reaction mixture, for agitation for 2 hours. The deposited crystal was filtered, rinsed in water and dried, to recover the listed compound D-29 as crystals in an amount of 7.9 g (yield of 96%).

1) Examples of Dyeing Performance of Dyestuffs

The dyes listed in Tables 1a and 1b were dissolved into a mainly aqueous formulation containing alkaline peroxide and applied in the form of a composition having the general formulation A to goat hair and human hair, respectively.

General Formulation A

| | |
|---|---|
| General Dyestuff (1) | 0.2 g |
| Benzyl Alcolohol | 5.0 g |
| Sodium Lauryl Sulphate | 0.01 g |
| Ammonium Hydroxide (25%) | 5.0 g |
| Hydrogen Peroxide (50%) | 6.0 g |
| Water | up to 100 g |
| pH | 10.0 |

The dye mixture was applied to undamaged white goat hair and undamaged human blonde hair at 50° C. for 15 min. 1.5–2.0 g of formulation A was applied per gram of hair. After the dyeing time (approx. 15 to 30 minutes) was complete, the tresses were rinsed with water, shampoo washed and then dried. The colour of the tresses was then recorded. L, a and b values of the tresses before and after the colouring treatment were measured by Minolta colour-measuring instrument and the value of delta E, which is a known measure for the chroma, was calculated according to the following equation:

$$\Delta E = (\Delta L^2 + \Delta a^2 + \Delta b^2)^{1/2}$$

for each example (this will apply equally to every example hereinafter).

The results are shown in Table 1a (Goat Hair) and Table 1b (Human Hair.)

TABLE 1a

Color on Undamaged White Goat Hair

| Dye Example | Colour of Dyed Hair | L | a | b | Delta E |
|---|---|---|---|---|---|
| D-89 | Bright Pink/Magenta | 53 | 44 | −16 | 63 |
| D-30 | Intense Magenta | 50 | 47 | −19 | 67 |
| D-37 | Dark Intense Magenta | 29 | 50 | −4 | 76 |
| D-41 | Intense Magenta | 35 | 57 | −9 | 79 |
| D-39 | Bright Violet | 29 | 48 | −25 | 83 |
| D-38 | Intense Red/Magenta | 44 | 57 | 6 | 70 |
| D-56 | Bright Intense Orange | 64 | 43 | 35 | 51 |
| D-46 | Bright Pink Red | 57 | 53 | 6 | 60 |
| D-29 | Bright Intense Red | 46 | 63 | 23 | 73 |
| D-43 | Intense Magenta | 49 | 50 | −8 | 65 |
| D-78 | Intense Yellow | 77 | 14 | 76 | 64 |
| D-79 | Intense Gold | 77 | 12 | 74 | 61 |
| D-80 | Intense Yellow | 79 | 11 | 57 | 45 |
| D-81 | Intense Yellow | 84 | −4 | 60 | 46 |
| D-82 | Intense Yellow | 77 | 7 | 76 | 63 |
| D-83 | Intense Yellow-Orange | 80 | 0 | 79 | 66 |
| D-84 | Very Intense Yellow | 79 | 8 | 84 | 71 |
| D-85 | Intense Cyan | 47 | 26 | −33 | 66 |
| D-86 | Intense Blue | 59 | −10 | −21 | 45 |
| D-87 | Intense Blue | 47 | −5 | −24 | 55 |
| D-88 | Intense Blue | 43 | −2 | −33 | 64 |
| D-91 | Bight Magenta | 38 | 61 | 3 | 77 |
| D-94 | Dark Magenta | 30 | 51 | −1 | 75 |
| D-95 | Bright Red | 51 | 52 | 14 | 62 |
| D-96 | Bright Yellow | 78 | 11 | 88 | 75 |
| D-97 | Dark Blue-Violet | 29 | 34 | −43 | 85 |
| D-98 | Dark Blue | 27 | 23 | −37 | 80 |

TABLE 1b

Color on Undamaged Human Blonde Hair

| Dye Example | Colour of Dyed Hair | L | a | b | Delta E |
|---|---|---|---|---|---|
| D-89 | Pink Red | 41 | 24 | 6 | 21 |
| D-30 | Dark Pink | 39 | 26 | 6 | 23 |
| D-37 | Intense Red Magenta | 29 | 33 | 3 | 33 |
| D-41 | Intense Pink Magenta | 30 | 35 | 1 | 35 |
| D-39 | Intense Violet | 27 | 26 | −7 | 34 |
| D-38 | Intense Red Pink | 34 | 33 | 10 | 29 |
| D-56 | Bright Intense Orange | 45 | 23 | 25 | 19 |
| D-46 | Bright Pink | 43 | 21 | 15 | 15 |
| D-29 | Bright Intense Red | 38 | 37 | 17 | 31 |
| D-43 | Intense Magenta | 37 | 29 | 8 | 24 |
| D-78 | Intense Yellow Gold | 68 | 6 | 31 | 26 |
| D-79 | Intense Gold | 56 | 9 | 40 | 25 |
| D-80 | Intense Yellow | 62 | 7 | 25 | 19 |
| D-81 | Intense Yellow Gold | 62 | 5 | 25 | 18 |
| D-82 | Intense Gold Yellow | 60 | 6 | 38 | 26 |
| D-83 | Intense Gold Orange | 71 | 2 | 19 | 26 |
| D-84 | Intense Yellow | 61 | 6 | 40 | 27 |
| D-85 | Intense Cyan | 36 | 10 | −1 | 20 |
| D-86 | Intense Blue | 44 | −8 | 8 | 17 |
| D-87 | Intense Blue | 38 | −8 | 0 | 23 |
| D-88 | Intense Blue | 33 | −8 | −6 | 29 |
| D-91 | Bright Magenta | 50 | 32 | 3 | 33 |
| D-94 | Dark Magenta | 46 | 23 | 1 | 36 |
| D-95 | Bright Red | 60 | 18 | 8 | 20 |
| D-96 | Bright Yellow | 58 | 8 | 46 | 32 |
| D-97 | Dark Blue-Violet | 29 | 5 | −12 | 34 |
| D-98 | Dark Blue | 32 | 8 | −11 | 35 |

2) Comparison with Anionic Dyes

The performance of dyes of the invention were compared with that of dyes not covered by the invention. Thus dyes D-82, A* and B* as shown below were used in the composition of the above mentioned general Formulation A and applied to undamaged white goat hair and undamaged human blonde hair for 15 mins at 50° C. (see Table 2a and 2b.)

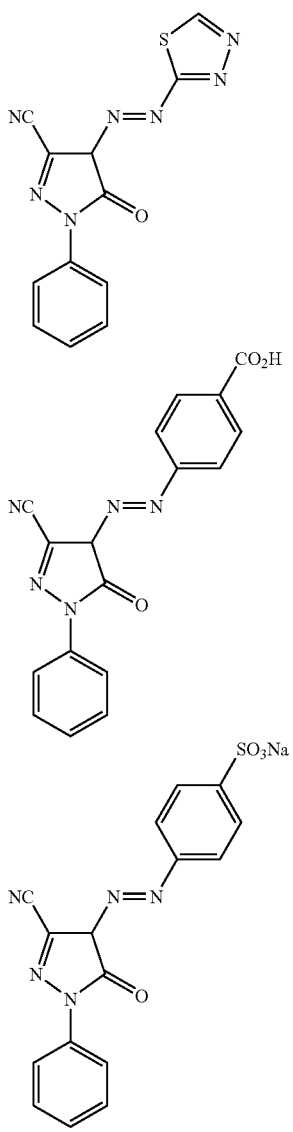

D-82

A*

B*

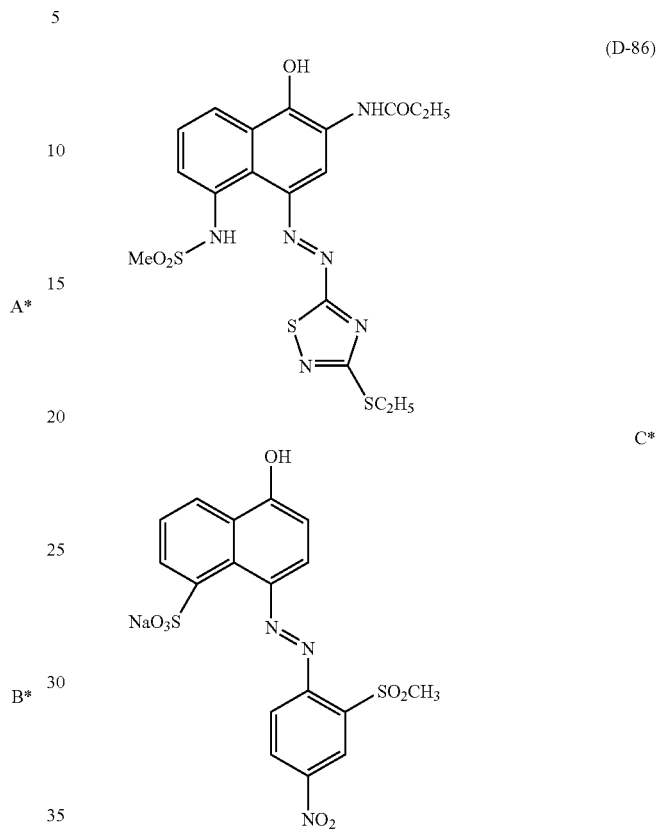

Similarly, the performance of (D-86) and (C)* were also compared by using the composition of the General Formulation A. The results are summarised in Table 3a and 3b.

TABLE 3a

Colour uptake on undamaged white goat hair

| Dye | Colour | L | a | b | Delta E |
|---|---|---|---|---|---|
| D-86 | Intense Violet Blue | 47 | 26 | −33 | 66 |
| C* | Pale Cyan | 65 | −13 | 2 | 23 |

*Not according to the invention

TABLE 2a

Colour uptake on undamaged white goat hair

| Dye | Colour | L | a | b | Delta E |
|---|---|---|---|---|---|
| D-82 | Very Intense Yellow | 77 | 7 | 76 | 63 |
| A* | Pale Yellow | 86 | −6 | 41 | 42 |
| B* | Pale Yellow | 85 | −5 | 42 | 43 |

*Not according to the invention

TABLE 2b

Colour uptake undamaged Blonde human hair

| Dye | Colour | L | a | b | Delta E |
|---|---|---|---|---|---|
| D-82 | Very Intense Gold | 53 | 10 | 44 | 26 |
| A* | Pale Yellow | 55 | 7 | 26 | 13 |
| B* | Pale Yellow | 55 | 6 | 26 | 13 |

*Not according to the invention

TABLE 3b

Colour uptake on undamaged Blonde human hair

| Dye | Colour | L | a | b | Delta E |
|---|---|---|---|---|---|
| D-86 | Violet Blue | 36 | 10 | −1 | 20 |
| C* | Pale Blonde | 51 | 2 | 19 | 7 |

*Not according to the invention

Clearly, the presence of a —COOH or a —SO$_3$H group, drastically reduces performance and thus these groups are excluded from the invention.

3) Examples of Wash Fade.

In order to assess the performance of the dyes of general formula I as defined, in terms of resistance to fading from washing, Dyes D-37 and D-41 were compared with a diazo dye containing a quaternary ammonium group (D)*.

* Not according to the invention

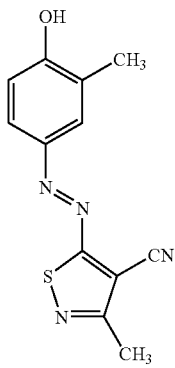

D-37

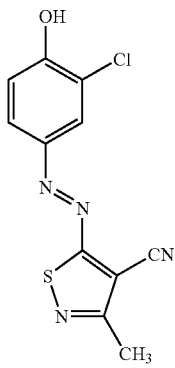

D-41

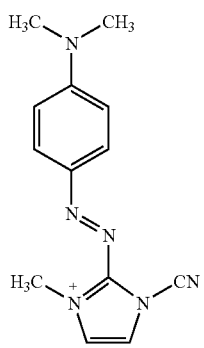

D*

Using the same formulation as described above (General Formulation A), the dyes were applied for 15 mins at 50° C. to damaged (permed) white goat hair. After the dyeing process was complete, the tresses were washed and dried and the colour noted. The tresses were then put through a wash fade protocol, to measure the resistance to shampoo washing.

The washing protocol consisted of applying 0.1 g of shampoo per 1 g of hair and milking into the hair for 30 seconds followed by rinsing the tresses for 30 seconds with 40 C water. This process was repeated 20 times. The tresses were then dried and the change in colour measured as a delta E value, using the Minolta Colorimeter. The results are shown in Table 4.

TABLE 4

Washfastness of Dye of the Invention compared to Cationic Dyes not of the invention

| Dye Example | Delta E fade from 20 Washes |
|---|---|
| D-37 | 4 |
| D-41 | 2 |
| Cationic Direct Dye* | 19 |

*Not according to the invention

Clearly, the presence of a quaternary ammonium group drastically reduces the durability of the dyestuffs to shampoo washing. Thus, these cationic substituents are excluded from the invention.

4) Performance in Combination with Persulphate and Peroxide:

The formulations shown in Table 5 were prepared and used to perform simultaneously a bleaching and a coloration treatment. The results of the evaluation are shown in Tables 6a and 6b.

TABLE 5

Formulations of the dye compositions

| Formulation | I* | II | III | IV | V | VI | VII | VIII | IX |
|---|---|---|---|---|---|---|---|---|---|
| D-84 | / | 0.75 | / | / | / | / | / | / | / |
| D-95 | / | / | 0.75 | / | / | / | / | / | / |
| D-118 | / | / | / | 0.75 | / | / | / | / | / |
| D-111 | / | / | / | / | 0.75 | / | / | / | / |
| D-110 | / | / | / | / | / | 0.75 | / | / | 0.4 |
| D-105 | / | / | / | / | / | / | 0.75 | / | / |
| D-100 | / | / | / | / | / | / | / | 0.75 | 0.35 |
| Ammonium persulphate | 7.3 | 7.3 | 7.3 | 7.3 | 7.3 | 7.3 | 7.3 | 7.3 | 7.3 |
| Potassium persulphate | 16.9 | 16.9 | 16.9 | 16.9 | 16.9 | 16.9 | 16.9 | 16.9 | 16.9 |
| Methylhydroxyethyl-cellulose | 3 | 3 | 3 | 3 | 3 | 3 | 3 | 3 | 3 |
| Sodium carbonate | 0.4 | 0.4 | 0.4 | 0.4 | 0.4 | 0.4 | 0.4 | 0.4 | 0.4 |
| Hydrogen peroxide (50%) | 6 | 6 | 6 | 6 | 6 | 6 | 6 | 6 | 6 |
| Ethanol | 2 | 2 | 2 | 2 | 2 | 2 | 2 | 2 | 2 |
| Benzyl Alcohol | 5 | 5 | 5 | 5 | 5 | 5 | 5 | 5 | 5 |

TABLE 5-continued

| | Formulations of the dye compositions | | | | | | | | |
|---|---|---|---|---|---|---|---|---|---|
| Formulation | I* | II | III | IV | V | VI | VII | VIII | IX |
| Water | ** | ** | ** | ** | ** | ** | ** | ** | ** |
| pH adjustment | 10 | 10 | 10 | 10 | 10 | 10 | 10 | 10 | 10 |

*Formulation not in accordance to the invention.
**Balance

Formulations I to IX were applied to undamaged white goat hair and undamaged dark brown human hair for 30 minutes at 30° C. After this time the tresses were washed and dried and then the colour change measured.

Results:

The examples dyed on undamaged white goat tresses in accordance to the invention II to VIII were intensely coloured showing that these dyes are surprisingly stable to persulphate plus peroxide bleaching conditions.

TABLE 6a

| | Untreated white goat hair | | | | |
|---|---|---|---|---|---|
| Formulation | L | A | B | Delta E | Colour |
| Initial | 82 | 0 | 12 | / | White |
| II | 78 | 4 | 69 | 55 | Intense Gold |
| III | 40 | 46 | 14 | 61 | Intense Red |
| IV | 55 | 5 | −10 | 36 | Ash Blue |
| V | 48 | 4 | −12 | 37 | Ash Blue |
| VI | 33 | 15 | −23 | 63 | Int. Blue Violet |
| VII | 48 | 50 | 7 | 60 | Int. Magenta-Red |
| VIII | 41 | 59 | 19 | 71 | Intense Red |

The examples dyed on undamaged dark brown human hair in accordance to the invention II to IX were significantly bleached and intensely coloured showing that these dyes are surprisingly stable to persulphate plus peroxide bleaching conditions allowing the hair to be simultaneously coloured and highly bleached.

TABLE 6b

| | Untreated dark brown human hair | | | |
|---|---|---|---|---|
| Formulation | L | a | B | Colour |
| Initial | 22 | 2 | 2 | Dark Brown |
| I* | 48 | 9 | 24 | Blonde |
| II | 43 | 9 | 34 | Intense Gold Blonde |
| III | 32 | 35 | 15 | Intense Copper Red |
| IV | 23 | 5 | 3 | Blue Ash Dark Blonde |
| V | 25 | 5 | 4 | Blue Ash Dark Blonde |
| VI | 23 | 5 | −3 | Violet Brown |
| VII | 34 | 31 | 12 | Intense Red |
| VIII | 30 | 39 | 15 | Intense Red |
| IX | 40 | 7 | 14 | Ash Blonde |
| X | 22 | 14 | 0 | Intense Violet |

*Control without dyestuffs - bleaching only.

5) Measurement of pKa Value pKa values of the azo dyes described below were determined by the following method; The dye was dissolved in a solution of a DMF/water (1/1) volume ratio to a final concentration of $2 \times 10^{-5}$ mol/l. After the resulting solution was adjusted to pH 2, using 1.0 mol/l hydrochloric acid, the solution was titrated with aqueous 1.0 mol/l sodium hydroxide solution. Recording the change of the visible ultra-violet absorption spectrum, the inflection point was determined by regression analysis. Table 7 shows the results.

TABLE 7

| | pKa values |
|---|---|
| Dye | pKa value determined |
| D-34 | 4.39 |
| D-30 | 3.05 |
| D-37 | 6.37 |
| D-40 | 4.46 |
| D-41 | 5.02 |
| D-39 | 5.52 |
| D-38 | 3.50 |
| D-45 | 2.28 |
| D-56 | 3.56 |
| D-46 | 5.15 |
| D-29 | 6.04 |
| D-43 | 3.90 |
| D-49 | 5.39 |

The invention claimed is:

1. Hair dye composition comprising at least one azo dye represented by the formula (1)

where A is selected from the following groups (A-1) to (A-18) and (A-20) to (A-25) which are monovalent hetero-ring groups binding via symbol * to the azo group:

(A-1)

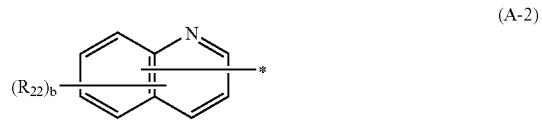

(A-2)

(A-3)

(A-4)

(A-5)

-continued (A-6) 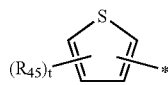

(A-7) 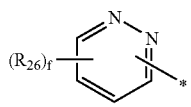

(A-8) 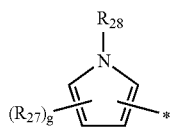

(A-9) 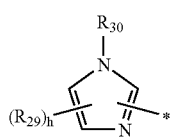

(A-10) 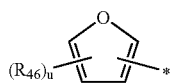

(A-11) 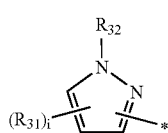

(A-12) 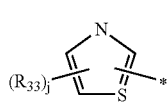

(A-13) 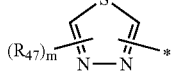

(A-14) 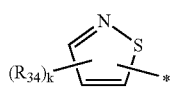

(A-15) 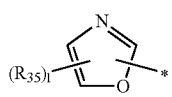

(A-16) 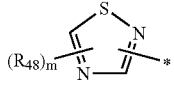

(A-17) 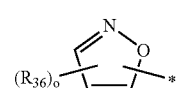

(A-18) 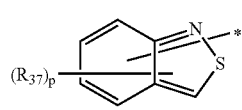

(A-20) 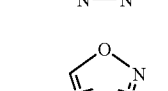

(A-21) 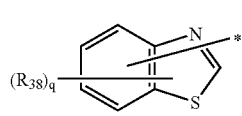

(A-22) 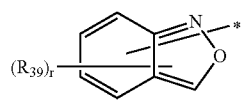

(A-23) 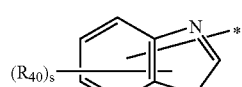

(A-24) 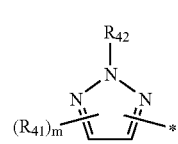

(A-25)

wherein; $R_{21}$ to $R_{42}$ and $R_{45}$ to $R_{50}$ independently represent hydrogen atom, halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; or wherein, groups adjacent to each other as represented by $R_{21}$ to $R_{42}$ and $R_{45}$ to $R_{50}$ can bind together to form a saturated or unsaturated 5- or 6-membered ring structure, "a, p, q, r, s" represent an integer of 0 to 4, "b, c" represent an integer of 0 to 6, "d, e, f, g, t, u" represent an integer of 0 to 3, "h, i, j, k, l, o" represent an integer of 0 to 2, "m" represent an integer of 0 to 1, wherein 2 or more groups represented by $R_{21}$ to $R_{42}$ and $R_{45}$ to $R_{50}$ in the same molecule can be the same or different to each other, and wherein when $R_{21}$ to $R_{42}$ and $R_{45}$ to $R_{50}$ in the formulas (A-1) to (A-18) and (A-20) to (A-25) are groups with a possibility of additional substitution, $R_{21}$ to $R_{42}$ and $R_{45}$ to $R_{50}$ can further contain a substituent and the substituents are the same as listed as $R_{21}$ to $R_{42}$ and $R_{45}$ to $R_{50}$ and B=heterocyclic, aromatic or alkyl group containing a dissociative proton and, which is free of carboxy (—$CO_2H$) or sulfo groups (—$SO_3H$) or quaternary ammonium groups; and wherein a pKa of the dye is in the range of 1.5 to 9.0.

2. Hair dye composition according to claim 1 wherein B is selected from the following groups (B-1) to (B-12) binding via symbol ** to the azo group:

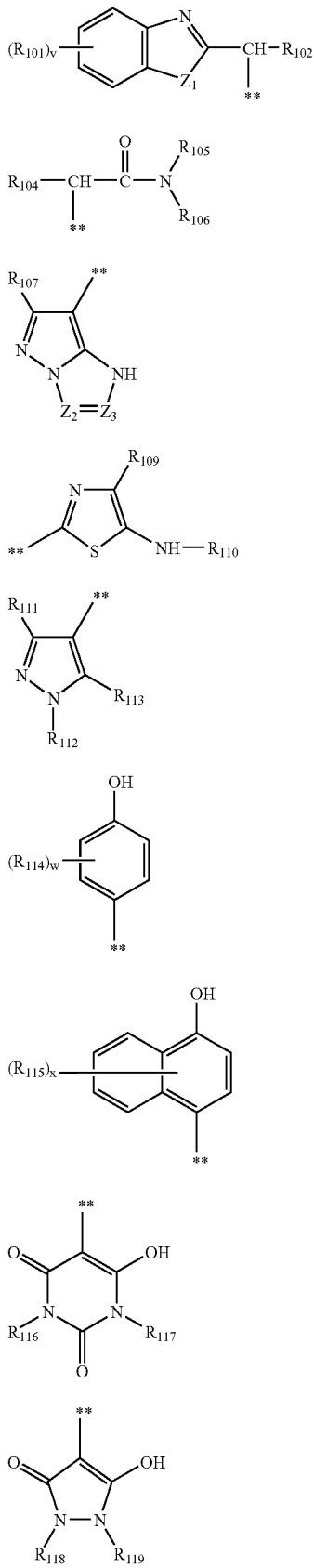
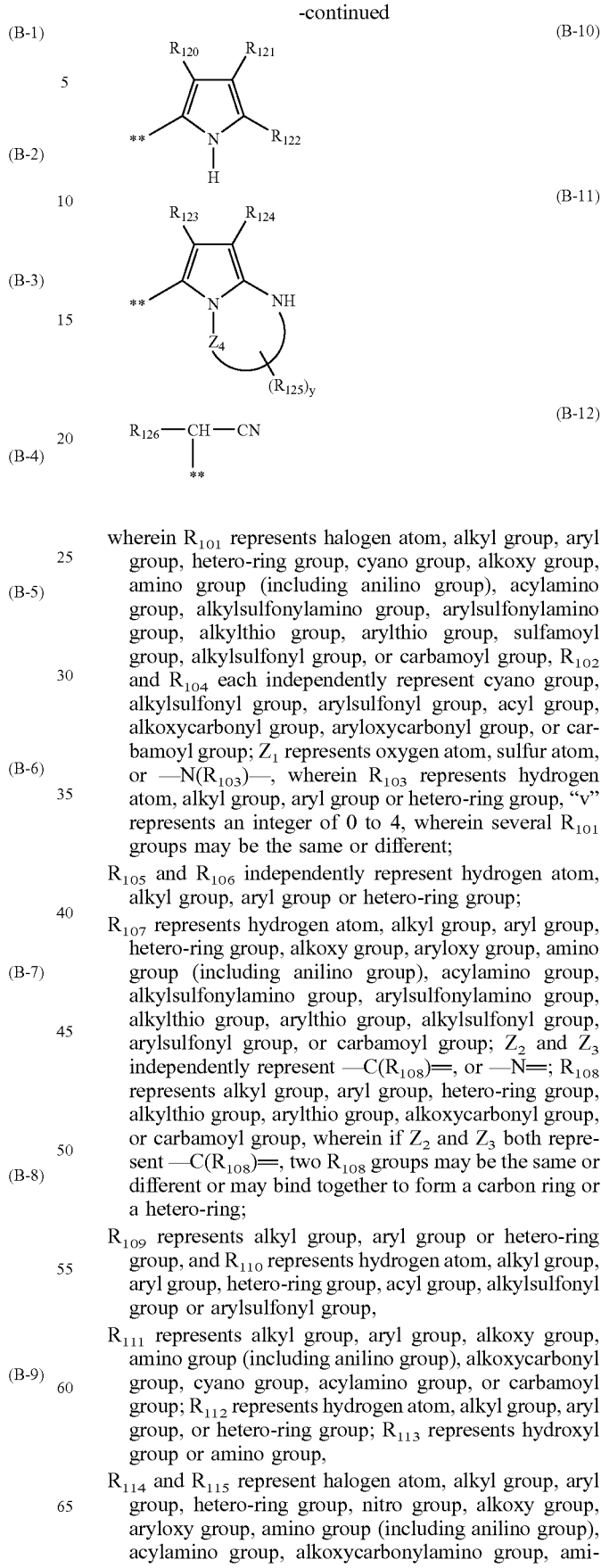

wherein $R_{101}$ represents halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group, $R_{102}$ and $R_{104}$ each independently represent cyano group, alkylsulfonyl group, arylsulfonyl group, acyl group, alkoxycarbonyl group, aryloxycarbonyl group, or carbamoyl group; $Z_1$ represents oxygen atom, sulfur atom, or —N($R_{103}$)—, wherein $R_{103}$ represents hydrogen atom, alkyl group, aryl group or hetero-ring group, "v" represents an integer of 0 to 4, wherein several $R_{101}$ groups may be the same or different;

$R_{105}$ and $R_{106}$ independently represent hydrogen atom, alkyl group, aryl group or hetero-ring group;

$R_{107}$ represents hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $Z_2$ and $Z_3$ independently represent —C($R_{108}$)=, or —N=; $R_{108}$ represents alkyl group, aryl group, hetero-ring group, alkylthio group, arylthio group, alkoxycarbonyl group, or carbamoyl group, wherein if $Z_2$ and $Z_3$ both represent —C($R_{108}$)=, two $R_{108}$ groups may be the same or different or may bind together to form a carbon ring or a hetero-ring;

$R_{109}$ represents alkyl group, aryl group or hetero-ring group, and $R_{110}$ represents hydrogen atom, alkyl group, aryl group, hetero-ring group, acyl group, alkylsulfonyl group or arylsulfonyl group, $R_{111}$ represents alkyl group, aryl group, alkoxy group, amino group (including anilino group), alkoxycarbonyl group, cyano group, acylamino group, or carbamoyl group; $R_{112}$ represents hydrogen atom, alkyl group, aryl group, or hetero-ring group; $R_{113}$ represents hydroxyl group or amino group, $R_{114}$ and $R_{115}$ represent halogen atom, alkyl group, aryl group, hetero-ring group, nitro group, alkoxy group, aryloxy group, amino group (including anilino group), acylamino group, alkoxycarbonylamino group, aminocarbonylamino group, alkylsulfonylamino group, arylsulfonylamino group, alkylthio group, arylthio group, hetero-ring thio group, alkoxycarbonyl group, or carbamoyl group; "w" represents an integer of 0 to 4, wherein several $R_{114}$ groups in the number "w" may be the same or different "x" represents an integer of 0 to 6, wherein several $R_{115}$ groups in the number "x" may be the same or different, $R_{116}$, $R_{117}$, $R_{118}$, and $R_{119}$ independently represent alkyl group or aryl group, $R_{120}$ and $R_{121}$ independently represent alkyl group, aryl group, hetero-ring group, cyano group, alkylsulfonyl group, arylsulfonyl group, alkoxycarbonyl group, or carbamoyl group; $R_{122}$ represents hydrogen atom, alkyl group, aryl group, hetero-ring group, acylamino group, alkylsulfonylamino group, or arylsulfonylamino group;

$R_{123}$ and $R_{124}$ independently represent alkyl group, aryl group, hetero-ring group, cyano group, alkylsulfonyl group, arylsulfonyl group, alkoxycarbonyl group, or carbamoyl group; $Z_4$ represents a non-metal atomic group forming a 5-membered or 6-membered ring, together with the two nitrogen atoms and one carbon atom, $R_{125}$ represents alkyl group, aryl group, alkoxy group, amino group, acylamino group, alkylsulfonylamino group, arylsulfonylamino group, alkylthio group, arylthio group, acyl group, alkoxycarbonyl group, or carbamoyl group; "y" represents an integer of 0 to 2, when $Z_4$ forms a 5-membered ring; and "y" represents an integer of 0 to 3, when $Z_4$ forms a 6-membered ring, $R_{126}$ represents alkyl group and aryl group, and wherein when $R_{101}$ to $R_{126}$ in the formulas (B-1) to (B-12) are groups with a possibility of additional substitution, $R_{101}$ to $R_{126}$ may further have a substituent, and the substituents are the same as listed as the substituent for the hetero-ring group represented by "A".

3. A hair dye composition according to any one of the claims 1 or 2 whereby the structure of the dye is represented by DS-1 to DS-9:

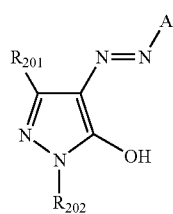

DS-1

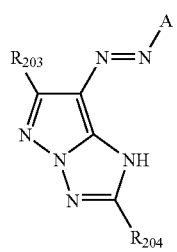

DS-2

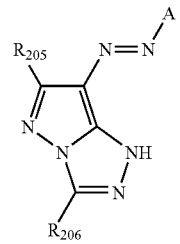

DS-3

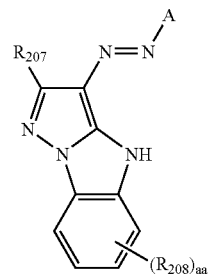

DS-4

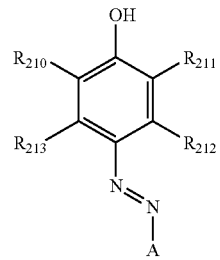

DS-5

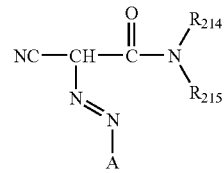

DS-6

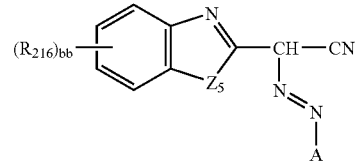

DS-7

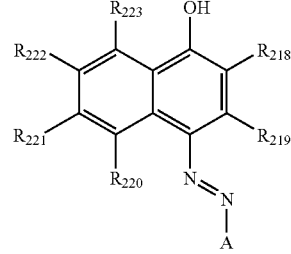

DS-8

DS-9 wherein "A" in the general formulas DS-1 to DS-9 has the same meaning as defined above, $R_{201}$ represents alkyl group, aryl group, alkoxy group, amino group (including anilino group), alkoxycarbonyl group, cyano group, acylamino group, or carbamoyl group; $R_{202}$ represents hydrogen atom, alkyl group, aryl group, or hetero-ring group, $R_{203}$, $R_{205}$ and $R_{207}$ independently represent hydrogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, or carbamoyl group; $R_{204}$ represents alkyl group, aryl group, or hetero-ring group, $R_{206}$ represents alkyl group, aryl group, hetero-ring group, alkylthio group, arylthio group, alkoxycarbonyl group, or carbamoyl group, $R_{208}$ represents halogen atom, alkyl group, aryl group, hetero-ring group, alkoxy group, aryloxy group, amino group (including anilino group), acylamino group, alkylsulfonylamino group, arylsulfonylamino group, alkylthio group, arylthio group, alkylsulfonyl group, arylsulfonyl group, alkoxycarbonyl group, or carbamoyl group; "aa" represents an integer of 0 to 4, wherein several $R_{208}$ groups in the number "aa" may be the same or different.

$R_{210}$ and $R_{211}$ independently represent hydrogen atom, halogen atom, alkyl group, aryl group, acylamino group, alkoxycarbonyl group, aminocarbonylamino group, alkylsulfonylamino group, arylsulfonylamino group, alkoxycarbonylamino group or carbamoyl group; wherein at least one of $R_{210}$ and $R_{211}$ is hydrogen atom, $R_{212}$ and $R_{213}$ represent hydrogen atom, halogen atom, alkyl group, alkoxy group, or acylamino group, $R_{214}$ and $R_{215}$ independently represent hydrogen atom, alkyl group, aryl group, or hetero-ring group, $R_{216}$ represents halogen atom, alkyl group, aryl group, hetero-ring group, cyano group, alkoxy group, amino group (including anilino group), acylamino group, alkylsulfonylamino group, arylsulfonylamino group, alkylthio group, arylthio group, sulfamoyl group, alkylsulfonyl group, or carbamoyl group; $Z_5$ represents oxygen atom, sulfur atom, or —N($R_{217}$)—, where $R_{217}$ represents hydrogen atom, aryl group, or hetero-ring group, "bb" represents an integer of 0 to 4, wherein several $R_{216}$ groups in the number "bb" may be the same or different, $R_{218}$ has the meaning of $R_{210}$, or sulfamoyl group; $R_{220}$ and $R_{223}$ represent hydrogen atom, halogen atom, acylamino group, alkoxycarbonylamino group, aminocarbonylamino group, alkylsulfonylamino group, or arylsulfonylamino group; $R_{219}$, $R_{221}$, and $R_{222}$ represent hydrogen atom, chlorine atom, bromine atom, alkyl group, and acylamino group, $R_{224}$ represents alkyl group or aryl group, wherein when $R_{201}$ to $R_{224}$ in the formulas DS-1 to DS-9 are groups with a possibility of additional substitution, $R_{201}$ to $R_{224}$ may have additional substituents, the substituents are the same as those listed in the description of the substituent for the hetero-ring group represented by "A".

4. Hair dyeing composition according to any one of the claims 1 or 2, wherein the azo dye of the formula (1) is present in an amount of 0.0001 to 20 wt. %, based on the whole composition.

5. The hair dyeing composition according to any one of the claims 1 or 2, further containing at least one direct dye other than the azo dye of general formula (1) and/or at least one oxidative dye.

6. The hair dyeing composition as claimed in claim 5, wherein the total amount of the dyes present in said composition is 0.001 to 20 wt. %, based on the whole composition.

7. The hair dyeing composition according to any one of the claims 1 or 2, further containing an alkaline agent in an amount of 0.01 to 20 wt. %, based on the whole composition.

8. The hair dyeing composition as defined in anyone of the claims 1 or 2, being a one part composition, a two part composition or a three part composition, wherein the two part composition comprises a first part containing an alkaline agent and a second part containing an oxidative agent, and wherein the three part composition contains the said first and second parts and additionally a third part containing a powdery oxidizing agent, wherein in each of the said composition the direct dye having the formula (1) may be contained in either one of the respective parts or in each part.

9. A method for dyeing human or animal hair, comprising applying the hair dye composition of claim 1 to the hair, rinsing the hair after completion of the dyeing and drying the hair.

* * * * *